United States Patent
Bhoo et al.

(10) Patent No.: US 9,580,479 B2
(45) Date of Patent: Feb. 28, 2017

(54) PEPTIDE TAG AND USES THEREOF

(71) Applicants: University-Industry Cooperation Group of Kyung Hee University, Yongin-si (KR); Myongji University Industry and Academia Cooperation Foundation, Yongin-si (KR)

(72) Inventors: Seong Hee Bhoo, Yongin-si (KR); Tae Ryong Hahn, Yongin-si (KR); Tae Lim Kim, Yongin-si (KR); Joo Won Suh, Yongin-si (KR); Seung Hwan Yang, Yongin-si (KR)

(73) Assignees: University—Industry Cooperation Group of Kyung Hee University (KR); Myongji University Industry and Academia Cooperation Foundation (KR)

( * ) Notice: Subject to any disclaimer, the term of this patent is extended or adjusted under 35 U.S.C. 154(b) by 0 days.

(21) Appl. No.: 14/415,685

(22) PCT Filed: Jun. 20, 2013

(86) PCT No.: PCT/KR2013/005432
§ 371 (c)(1),
(2) Date: Jan. 19, 2015

(87) PCT Pub. No.: WO2014/014206
PCT Pub. Date: Jan. 23, 2014

(65) Prior Publication Data
US 2015/0175669 A1    Jun. 25, 2015

(30) Foreign Application Priority Data

Jul. 20, 2012  (KR) ................. 10-2012-0079615
Nov. 6, 2012   (KR) ................. 10-2012-0124732

(51) Int. Cl.
| | | |
|---|---|---|
| *C07K 14/195* | (2006.01) | |
| *G01N 33/58* | (2006.01) | |
| *G01N 33/68* | (2006.01) | |
| *G01N 33/573* | (2006.01) | |
| *C07K 14/435* | (2006.01) | |
| *C07K 19/00* | (2006.01) | |
| *C12N 15/11* | (2006.01) | |
| *C12N 15/31* | (2006.01) | |
| *C12N 9/10* | (2006.01) | |
| *C07K 7/06* | (2006.01) | |
| *C07K 1/22* | (2006.01) | |
| *C07K 16/12* | (2006.01) | |

(52) U.S. Cl.
CPC .............. *C07K 14/195* (2013.01); *C07K 1/22* (2013.01); *C07K 14/43595* (2013.01); *C07K 16/12* (2013.01); *C12N 9/1088* (2013.01); *G01N 33/573* (2013.01); *G01N 33/58* (2013.01); *G01N 33/68* (2013.01); *G01N 33/6803* (2013.01); *C07K 2317/33* (2013.01); *C07K 2317/34* (2013.01); *C07K 2319/00* (2013.01); *C07K 2319/40* (2013.01); *C07K 2319/60* (2013.01); *G01N 2333/195* (2013.01); *G01N 2333/43595* (2013.01); *G01N 2333/91177* (2013.01)

(58) Field of Classification Search
None
See application file for complete search history.

(56) References Cited

U.S. PATENT DOCUMENTS

| | | | |
|---|---|---|---|
| 6,462,254 | B1 | 10/2002 | Vernachio et al. |
| 7,135,624 | B2 | 11/2006 | Bryan et al. |
| 7,361,462 | B2 | 4/2008 | Satoh et al. |
| 7,951,559 | B2 | 5/2011 | Alsop et al. |
| 2005/0221308 | A1 | 10/2005 | Samaddar et al. |
| 2006/0099710 | A1 | 5/2006 | Donnelly et al. |
| 2010/0184612 | A1 | 7/2010 | Rondon et al. |

FOREIGN PATENT DOCUMENTS

| | | | |
|---|---|---|---|
| JP | 2007252372 | A | 10/2007 |
| WO | 8807085 | A1 | 9/1988 |
| WO | 8807086 | A1 | 9/1988 |
| WO | 8809344 | A1 | 12/1988 |
| WO | WO 03/089652 | * | 10/2003 |
| WO | WO 2009/009562 | * | 1/2009 |

OTHER PUBLICATIONS

Uniprot Accession Q9RZA4, 2001.*
English translation of Kim et al. J. Appl. Biol. Chem, 53(2), 112-115, 2010.*
Bhoo, S.H. et al., Bacteriophytochromes are photochromic histidine kinases using a biliverdin chromophore, Nature, vol. 414, Dec. 13, 2001, pp. 776-779.
Davis, S.J. et al., Bacteriophytochromes: Phytochrome-Like Photoreceptors from Nonphotosynthetic Eubacteria, Science, vol. 286, Dec. 24, 1999, pp. 2517-2520.
(Continued)

*Primary Examiner* — Oluwatosin Ogunbiyi
(74) *Attorney, Agent, or Firm* — The Webb Law Firm

(57) ABSTRACT

There are provided peptide tags derived from bacteriophytochrome (BphP) that is photoreceptor protein of *Deinococcus radiodurans*, an antibody capable of specifically recognizing the peptide tags, hybridoma cell lines capable of producing the antibody, and uses thereof. The novel peptide tag has advantages in that it has a short length and can remove a non-specific reaction of the conventional c-myc tag and FLAG tag. Therefore, in the case of using the novel peptide tag and antibody thereto, the fusion protein expressed in a recombinant cell can be very effectively detected or purified. In addition, an epitope tagging system including the novel peptide tag and antibody thereto can be applied in various fields such as a determination of an intracellular site, a confirmation of functionality, detection and purification of specific protein, and researches on interaction between proteins.

4 Claims, 4 Drawing Sheets

(56) References Cited

OTHER PUBLICATIONS

Evan, G.I. et al., Isolation of Monoclonal Antibodies Specific for Human c-myc Proto-Oncogene Product, Mol. Cell. Biol., vol. 5, No. 12, Dec. 1985, pp. 3610-3616.

Field, J. et al., Purification of a RAS-Responsive Adenylyl Cyclase Complex from *Saccharmyces cerevisiae* by Use of an Epitope Addition Method, Mol. Cell. Biol., vol. 8, No. 5, May 1988, pp. 2159-2165.

Gasic, K. et al., Nonspecific Binding of Monoclonal Anti-FLAG M2 Antibody in Indian Mustard (*Brassica juncea*), Plant Molecular Biology Reporter, vol. 23, Mar. 2005, pp. 9-16.

Giraud, E. et al., Bacteriophytochromes in anoxygenic photosynthetic bacteria, Photosynth Res, vol. 97, Jul. 9, 2008, pp. 141-153.

Hopp, T.P. et al., A Short Polypeptide Marker Sequence Useful for Recombinant Protein Identification and Purification, Bio/Technology, vol. 6, 1988, pp. 1204-1210.

Izsvak, Z. et al., Sleeping Beauty, a Wide Host-range Transposon Vector for Genetic Transformation in Vertebrates, J. Mol. Biol., vol. 302, 2000, pp. 93-102.

Kim, T.L. et. al., Production of Bacteriophytochrome Specific Antibodies of Deinococcus radiodurans, J. Appl. Biol. Chem., vol. 53, No. 2, 2010, pp. 112-115—English Abstract.

Konigsberg, W. et al., Evidence for use of rare codons in the dnaG gene and other regulatory genes of *Escherichia coli*, Proc. Nat'l. Acad. Sci. U.S.A. vol. 80, Feb. 1983, pp. 687-691.

Lipton, M.S. et. al., Global analysis of the Deinococcus radiodurans proteome by using accurate mass tags, PNAS, Aug. 20, 2002, vol. 99, No. 17, pp. 11049-11054.

Rigaut, G. et al., A generic protein purification method for protein complex characterization and proteome exploration, Nat Biotechnol, vol. 17, Oct. 1999, pp. 1030-1032.

Rockwell, N.C. et al., Phytochome Structure and Signaling Mechanisms, Annu Rev Plant Biol, vol. 57, 2006, pp. 837-858.

Sparkes, I.A. et al., Rapid, transient expression of fluorescent fusion proteins in tobacco plants and generation of stably transformed plants, Nature Protocols, Nov. 30, 2006, vol. 1, No. 4, pp. 2019-2025.

Stevens, R.C., Design of high-throughput methods of protein production for structural biology, Structure, 2000, vol. 8, No. 9, pp. R177-R185.

Vierstra, R.D. et al., Bacteriophytochromes: new tools for understanding phytochrome signal transduction, Seminars in Cell Dev Biol, 2000, vol. 11, pp. 511-521.

\* cited by examiner

US 9,580,479 B2

SEQUENCE LISTING

<160> NUMBER OF SEQ ID NOS: 57

<210> SEQ ID NO 1
<211> LENGTH: 9
<212> TYPE: PRT
<213> ORGANISM: Artificial Sequence
<220> FEATURE:
<223> OTHER INFORMATION: Deinococcus radiodurans BphP 3-11 a.a.

<400> SEQUENCE: 1

Arg Asp Pro Leu Pro Phe Phe Pro Pro
1               5

<210> SEQ ID NO 2
<211> LENGTH: 9
<212> TYPE: PRT
<213> ORGANISM: Artificial Sequence
<220> FEATURE:
<223> OTHER INFORMATION: 8th Phe-substituted Deinococcus radiodurans
      BphP 3-11 a.a.

<400> SEQUENCE: 2

Arg Asp Pro Leu Pro Ala Phe Pro Pro
1               5

<210> SEQ ID NO 3
<211> LENGTH: 755
<212> TYPE: PRT
<213> ORGANISM: Deinococcus radiodurans

<400> SEQUENCE: 3

Met Ser Arg Asp Pro Leu Pro Phe Phe Pro Pro Leu Tyr Leu Gly Gly
1               5                   10                  15

Pro Glu Ile Thr Thr Glu Asn Cys Glu Arg Glu Pro Ile His Ile Pro
            20                  25                  30

Gly Ser Ile Gln Pro His Gly Ala Leu Leu Thr Ala Asp Gly His Ser
        35                  40                  45

Gly Glu Val Leu Gln Met Ser Leu Asn Ala Ala Thr Phe Leu Gly Gln
    50                  55                  60

Glu Pro Thr Val Leu Arg Gly Gln Thr Leu Ala Ala Leu Leu Pro Glu
65                  70                  75                  80

Gln Trp Pro Ala Leu Gln Ala Ala Leu Pro Pro Gly Cys Pro Asp Ala
                85                  90                  95

Leu Gln Tyr Arg Ala Thr Leu Asp Trp Pro Ala Ala Gly His Leu Ser
            100                 105                 110

Leu Thr Val His Arg Val Gly Glu Leu Leu Ile Leu Glu Phe Glu Pro
        115                 120                 125

Thr Glu Ala Trp Asp Ser Thr Gly Pro His Ala Leu Arg Asn Ala Met
    130                 135                 140

Phe Ala Leu Glu Ser Ala Pro Asn Leu Arg Ala Leu Ala Glu Val Ala
145                 150                 155                 160

Thr Gln Thr Val Arg Glu Leu Thr Gly Phe Asp Arg Val Met Leu Tyr
                165                 170                 175

Lys Phe Ala Pro Asp Ala Thr Gly Glu Val Ile Ala Glu Ala Arg Arg
            180                 185                 190

Glu Gly Leu His Ala Phe Leu Gly His Arg Phe Pro Ala Ser Asp Ile
        195                 200                 205

Pro Ala Gln Ala Arg Ala Leu Tyr Thr Arg His Leu Leu Arg Leu Thr
    210                 215                 220

-continued

```
Ala Asp Thr Arg Ala Ala Val Pro Leu Asp Pro Val Leu Asn Pro
225                 230                 235                 240

Gln Thr Asn Ala Pro Thr Pro Leu Gly Gly Ala Val Leu Arg Ala Thr
            245                 250                 255

Ser Pro Met His Met Gln Tyr Leu Arg Asn Met Gly Val Gly Ser Ser
        260                 265                 270

Leu Ser Val Ser Val Val Gly Gly Gln Leu Trp Gly Leu Ile Ala
    275                 280                 285

Cys His His Gln Thr Pro Tyr Val Leu Pro Pro Asp Leu Arg Thr Thr
    290                 295                 300

Leu Glu Tyr Leu Gly Arg Leu Leu Ser Leu Gln Val Gln Val Lys Glu
305                 310                 315                 320

Ala Ala Asp Val Ala Ala Phe Arg Gln Ser Leu Arg Glu His His Ala
                325                 330                 335

Arg Val Ala Leu Ala Ala His Ser Leu Ser Pro His Asp Thr Leu
                340                 345                 350

Ser Asp Pro Ala Leu Asp Leu Leu Gly Leu Met Arg Ala Gly Gly Leu
            355                 360                 365

Ile Leu Arg Phe Glu Gly Arg Trp Gln Thr Leu Gly Glu Val Pro Pro
370                 375                 380

Ala Pro Ala Val Asp Ala Leu Leu Ala Trp Leu Glu Thr Gln Pro Gly
385                 390                 395                 400

Ala Leu Val Gln Thr Asp Ala Leu Gly Gln Leu Trp Pro Ala Gly Ala
                405                 410                 415

Asp Leu Ala Pro Ser Ala Ala Gly Leu Leu Ala Ile Ser Val Gly Glu
            420                 425                 430

Gly Trp Ser Glu Cys Leu Val Trp Leu Arg Pro Glu Leu Arg Leu Glu
    435                 440                 445

Val Ala Trp Gly Gly Ala Thr Pro Asp Gln Ala Lys Asp Asp Leu Gly
    450                 455                 460

Pro Arg His Ser Phe Asp Thr Tyr Leu Glu Glu Lys Arg Gly Tyr Ala
465                 470                 475                 480

Glu Pro Trp His Pro Gly Glu Ile Glu Glu Ala Gln Asp Leu Arg Asp
                485                 490                 495

Thr Leu Thr Gly Ala Leu Gly Glu Arg Leu Ser Val Ile Arg Asp Leu
            500                 505                 510

Asn Arg Ala Leu Thr Gln Ser Asn Ala Glu Trp Arg Gln Tyr Gly Phe
        515                 520                 525

Val Ile Ser His His Met Gln Glu Pro Val Arg Leu Ile Ser Gln Phe
    530                 535                 540

Ala Glu Leu Leu Thr Arg Gln Pro Arg Ala Gln Asp Gly Ser Pro Asp
545                 550                 555                 560

Ser Pro Gln Thr Glu Arg Ile Thr Gly Phe Leu Leu Arg Glu Thr Ser
                565                 570                 575

Arg Leu Arg Ser Leu Thr Gln Asp Leu His Thr Tyr Thr Ala Leu Leu
            580                 585                 590

Ser Ala Pro Pro Pro Val Arg Arg Pro Thr Pro Leu Gly Arg Val Val
        595                 600                 605

Asp Asp Val Leu Gln Asp Leu Glu Pro Arg Ile Ala Asp Thr Gly Ala
    610                 615                 620

Ser Ile Glu Val Ala Pro Glu Leu Pro Val Ile Ala Ala Asp Ala Gly
625                 630                 635                 640

Leu Leu Arg Asp Leu Leu Leu His Leu Ile Gly Asn Ala Leu Thr Phe
```

|  | 645 |  |  |  | 650 |  |  |  |  | 655 |  |  |
|---|---|---|---|---|---|---|---|---|---|---|---|---|

Gly Gly Pro Glu Pro Arg Ile Ala Val Arg Thr Glu Arg Gln Gly Ala
              660                 665                 670

Gly Trp Ser Ile Ala Val Ser Asp Gln Gly Ala Gly Ile Ala Pro Glu
          675                 680                 685

Tyr Gln Glu Arg Ile Phe Leu Leu Phe Gln Arg Leu Gly Ser Leu Asp
      690                 695                 700

Glu Ala Leu Gly Asn Gly Leu Gly Leu Pro Leu Cys Arg Lys Ile Ala
705                 710                 715                 720

Glu Leu His Gly Gly Thr Leu Thr Val Glu Ser Ala Pro Gly Glu Gly
              725                 730                 735

Ser Thr Phe Arg Cys Trp Leu Pro Asp Ala Gly Pro Leu Pro Gly Ala
          740                 745                 750

Ala Asp Ala
      755

<210> SEQ ID NO 4
<211> LENGTH: 2268
<212> TYPE: DNA
<213> ORGANISM: Deinococcus radiodurans

<400> SEQUENCE: 4

```
atgagccggg acccgttgcc cttttttcca ccgctttacc ttggtggccc ggaaattacc      60
accgagaact gcgagcgcga gccgattcat attcccggca gcatccagcc gcacggcgcc     120
ctgctcactg ccgacgggca cagcggcgag gtgctccaga tgagcctcaa cgcggccact     180
tttctgggac aggaacccac agtgctgcgc ggacagaccc tcgccgcact gctgcccgag     240
cagtggcccg cgctgcaagc ggccctgccc ccggctgcc ccgacgccct gcaataccgc      300
gcaacgctgg actggcctgc cgccgggcac cttttcgctga cggtgcaccg ggtcggcgag     360
ttgctgattc tggaattcga gccgacgag gcctgggaca gcaccgggcc gcacgcgctg      420
cgcaacgcga tgttcgcgct cgaaagtgcc cccaacctgc gggcgctggc cgaggtggcg     480
acccagacgg tccgcgagct gacgggcttt gaccgggtga tgctctacaa atttgccccc     540
gacgccaccg gcgaagtgat tgccgaggcc cgccgtgagg ggctgcacgc ctttctgggc     600
caccgttttc ccgcgtcgga cattccggcg caggcccgcg cgctctacac ccggcacctg     660
ctgccgctga ccgccgacac ccgcgccgcc gccgtgccgc tcgatcccgt cctcaacccg     720
cagacgaatg cgcccacccc gctgggcggc gccgtgctgc cgccaccctc gcccatgcac     780
atgcagtacc tgcggaacat gggcgtcggg tcgagcctgt cggtgtcggt ggtggtcggc     840
ggccagctct ggggcctgat cgcctgccac caccagacgc cctacgtgtt ccgcccgac      900
ctgcgaacca cgctcgaata cctgggccgc ttgctgagcc tgcaagttca ggtcaaggaa     960
gcggcggacg tggcggcctt cgccagagc ctgcgggagc accacgcgcg ggtggccctc     1020
gcggcggcgc actcgctctc gccgcacgac accctcagtg accggcgct tgacctgctg     1080
ggcctgatgc gggccggggg cctgattctg cgtttcgagg ccgctggca gacgttgggt     1140
gaagtgccgc ctgccccggc ggtgacgcg ctgctggcgt ggctcgaaac ccagccgggc     1200
gccctggtcc agaccgacgc gctgggccaa ctgtggcccg ccggcgccga tctcgccccc     1260
agcgcagcgg cctgctcgc catcagcgtg gcgagggct ggtcggagtg cctcgtctgg     1320
ctgcggcccg aactgcggct ggaggtcgcc tgggcggg ccactcctga ccaggcgaaa       1380
gacgacctcg ggccgcgcca ctcattcgac acctacctcg aagaaaaacg cggctacgcc     1440
```

| | | |
|---|---|---|
| gagccctggc atcccggcga aatcgaggag gcgcaggatc tacgtgacac attgaccggg | 1500 | |
| gcgctgggcg agcgcctgag cgtgattcgt gacctcaacc gggcgctcac acagtcgaac | 1560 | |
| gccgagtggc ggcagtacgg cttcgttatc agccaccaca tgcaggagcc ggtgcggctc | 1620 | |
| atctcgcagt tcgccgagtt gctgacgcgc agccccgcg cccaggacgg gtctccggac | 1680 | |
| tctccgcaga ccgagcgcat caccggcttt ctgctgcgcg aaacgtcgcg cctgcgcagc | 1740 | |
| ctgacgcaag acctccacac ctacaccgcg ctgctctcgg caccgccgcc ggtgcgccgc | 1800 | |
| cccacgccgc tgggccgcgt ggtggacgat gtgctgcaag acctcgaacc ccgcattgcc | 1860 | |
| gacaccggag cgagcatcga ggtggcgccc gagttgcccg tcatcgctgc cgacgctggc | 1920 | |
| ctgctgcgcg acctgctgct gcatctgatc ggcaacgcgc tgacgtttgg tggcccggag | 1980 | |
| ccgcgtattg ccgtaaggac cgaacggcaa ggcgcgggtt ggtctatcgc ggtcagtgac | 2040 | |
| cagggcgctg gcatcgcgcc cgagtatcag gaacgaatct ttctgctgtt tcagcggctc | 2100 | |
| ggttcgctcg atgaggcgct gggcaacggc ctgggcctgc cgctgtgccg caagatcgcc | 2160 | |
| gaactgcatg gcggcaccct gaccgtggag tccgcgccag gcgagggcag caccttccgt | 2220 | |
| tgctggctgc ccgatgctgg gcctcttccg ggagccgccg atgcctga | 2268 | |

<210> SEQ ID NO 5
<211> LENGTH: 963
<212> TYPE: DNA
<213> ORGANISM: Deinococcus radiodurans

<400> SEQUENCE: 5

| | | |
|---|---|---|
| atgagccggg acccgttgcc ctttttttcca ccgctttacc ttggtggccc ggaaattacc | 60 | |
| accgagaact gcgagcgcga gccgattcat attcccggca gcatccagcc gcacggcgcc | 120 | |
| ctgctcactg ccgacgggca cagcggcgag gtgctccaga tgagcctcaa cgcggccact | 180 | |
| tttctgggac aggaacccac agtgctgcgc ggacagaccc tcgccgcact gctgcccgag | 240 | |
| cagtggcccg cgctgcaagc ggccctgccc ccggctgcc ccgacgccct gcaataccgc | 300 | |
| gcaacgctgg actggcctgc cgccgggcac cttttcgctga cggtgcaccg ggtcggcgag | 360 | |
| ttgctgattc tggaattcga gccgacggag gcctgggaca gcaccgggcc gcacgcgctg | 420 | |
| cgcaacgcga tgttcgcgct cgaaagtgcc cccaacctgc gggcgctggc cgaggtggcg | 480 | |
| acccagacgg tccgcgagct gacgggcttt gaccgggtga tgctctacaa atttgccccc | 540 | |
| gacgccaccg gcgaagtgat tgccgaggcc cgccgtgagg ggctgcacgc ctttctgggc | 600 | |
| caccgttttc ccgcgtcgga cattccggcg caggcccgcg cgctctacac ccggcacctg | 660 | |
| ctgcgcctga ccgccgacac ccgcgccgcc gccgtgccgc tcgatcccgt cctcaacccg | 720 | |
| cagacgaatg cgcccacccc gctgggcggc gccgtgctgc gcgccacctc gcccatgcac | 780 | |
| atgcagtacc tgcggaacat gggcgtcggg tcgagcctgt cggtgtcggt ggtggtcggc | 840 | |
| ggccagctct ggggcctgat cgcctgccac caccagacgc cctacgtgtt gccgcccgac | 900 | |
| ctgcgaacca cgctcgaata cctgggccgc ttgctgagcc tgcaagttca ggtcaaggaa | 960 | |
| gcg | 963 | |

<210> SEQ ID NO 6
<211> LENGTH: 321
<212> TYPE: PRT
<213> ORGANISM: Deinococcus radiodurans

<400> SEQUENCE: 6

Met Ser Arg Asp Pro Leu Pro Phe Phe Pro Pro Leu Tyr Leu Gly Gly

```
  1               5                  10                 15
Pro Glu Ile Thr Thr Glu Asn Cys Glu Arg Glu Pro Ile His Ile Pro
                    20                 25                 30

Gly Ser Ile Gln Pro His Gly Ala Leu Leu Thr Ala Asp Gly His Ser
            35                 40                 45

Gly Glu Val Leu Gln Met Ser Leu Asn Ala Ala Thr Phe Leu Gly Gln
        50                 55                 60

Glu Pro Thr Val Leu Arg Gly Gln Thr Leu Ala Ala Leu Leu Pro Glu
 65                 70                 75                 80

Gln Trp Pro Ala Leu Gln Ala Ala Leu Pro Pro Gly Cys Pro Asp Ala
                85                 90                 95

Leu Gln Tyr Arg Ala Thr Leu Asp Trp Pro Ala Ala Gly His Leu Ser
               100                105                110

Leu Thr Val His Arg Val Gly Glu Leu Ile Leu Glu Phe Glu Pro
               115                120                125

Thr Glu Ala Trp Asp Ser Thr Gly Pro His Ala Leu Arg Asn Ala Met
130                135                140

Phe Ala Leu Glu Ser Ala Pro Asn Leu Arg Ala Leu Ala Glu Val Ala
145                150                155                160

Thr Gln Thr Val Arg Glu Leu Thr Gly Phe Asp Arg Val Met Leu Tyr
               165                170                175

Lys Phe Ala Pro Asp Ala Thr Gly Glu Val Ile Ala Glu Ala Arg Arg
               180                185                190

Glu Gly Leu His Ala Phe Leu Gly His Arg Phe Pro Ala Ser Asp Ile
               195                200                205

Pro Ala Gln Ala Arg Ala Leu Tyr Thr Arg His Leu Leu Arg Leu Thr
210                215                220

Ala Asp Thr Arg Ala Ala Val Pro Leu Asp Pro Val Leu Asn Pro
225                230                235                240

Gln Thr Asn Ala Pro Thr Pro Leu Gly Gly Ala Val Leu Arg Ala Thr
               245                250                255

Ser Pro Met His Met Gln Tyr Leu Arg Asn Met Gly Val Gly Ser Ser
               260                265                270

Leu Ser Val Ser Val Val Gly Gln Leu Trp Gly Leu Ile Ala
               275                280                285

Cys His His Gln Thr Pro Tyr Val Leu Pro Pro Asp Leu Arg Thr Thr
               290                295                300

Leu Glu Tyr Leu Gly Arg Leu Leu Ser Leu Gln Val Gln Val Lys Glu
305                310                315                320

Ala

<210> SEQ ID NO 7
<211> LENGTH: 27
<212> TYPE: DNA
<213> ORGANISM: Artificial Sequence
<220> FEATURE:
<223> OTHER INFORMATION: Nucleotides for Deinococcus radiodurans BphP
      3-11 a.a.

<400> SEQUENCE: 7
cgggacccgt tgcccttttt tccaccg                                         27

<210> SEQ ID NO 8
<211> LENGTH: 27
<212> TYPE: DNA
<213> ORGANISM: Artificial Sequence
```

```
<220> FEATURE:
<223> OTHER INFORMATION: Nucleotides for 8th Phe-substituted Deinococcus
      radiodurans BphP 3-11 a.a.

<400> SEQUENCE: 8
cgggacccgt tgcccgcctt tccaccg                                              27

<210> SEQ ID NO 9
<211> LENGTH: 29
<212> TYPE: DNA
<213> ORGANISM: Artificial Sequence
<220> FEATURE:
<223> OTHER INFORMATION: Forward primer for Deinococcus radiodurans BphP

<400> SEQUENCE: 9
gccatatgat gagccgggac ccgttgccc                                            29

<210> SEQ ID NO 10
<211> LENGTH: 29
<212> TYPE: DNA
<213> ORGANISM: Artificial Sequence
<220> FEATURE:
<223> OTHER INFORMATION: Reverse primer for Deinococcus radiodurans BphP

<400> SEQUENCE: 10
gcctcgagtc aggcatcggc ggctcccgg                                            29

<210> SEQ ID NO 11
<211> LENGTH: 29
<212> TYPE: DNA
<213> ORGANISM: Artificial Sequence
<220> FEATURE:
<223> OTHER INFORMATION: Forward primer for Deinococcus radiodurans BphP
      1-321 a.a.

<400> SEQUENCE: 11
gccatatgat gagccgggac ccgttgccc                                            29

<210> SEQ ID NO 12
<211> LENGTH: 29
<212> TYPE: DNA
<213> ORGANISM: Artificial Sequence
<220> FEATURE:
<223> OTHER INFORMATION: Reverse primer for Deinococcus radiodurans BphP
      1-321 a.a.

<400> SEQUENCE: 12
gcctcgagcg cttccttgac ctgaacttg                                            29

<210> SEQ ID NO 13
<211> LENGTH: 10
<212> TYPE: PRT
<213> ORGANISM: Artificial Sequence
<220> FEATURE:
<223> OTHER INFORMATION: Deinococcus radiodurans BphP 3-12 a.a.

<400> SEQUENCE: 13

Arg Asp Pro Leu Pro Phe Phe Pro Pro Leu
1               5                   10

<210> SEQ ID NO 14
<211> LENGTH: 38
<212> TYPE: DNA
<213> ORGANISM: Artificial Sequence
<220> FEATURE:
<223> OTHER INFORMATION: Forward primer for Deinococcus radiodurans BphP
      3-12 a.a.
```

-continued

<400> SEQUENCE: 14
gcctcgaggg atccatgcgg gacccgttgc ccttttttt                                38

<210> SEQ ID NO 15
<211> LENGTH: 38
<212> TYPE: DNA
<213> ORGANISM: Artificial Sequence
<220> FEATURE:
<223> OTHER INFORMATION: Reverse primer for Deinococcus radiodurans BphP
      3-12 a.a.

<400> SEQUENCE: 15
gcgagctcga attctcaaag cggtggaaaa aagggcaa                                 38

<210> SEQ ID NO 16
<211> LENGTH: 38
<212> TYPE: DNA
<213> ORGANISM: Artificial Sequence
<220> FEATURE:
<223> OTHER INFORMATION: Forward primer for Deinococcus radiodurans BphP
      3-11 a.a.

<400> SEQUENCE: 16
gcctcgaggg atccatgcgg gacccgttgc ccttttttt                                38

<210> SEQ ID NO 17
<211> LENGTH: 38
<212> TYPE: DNA
<213> ORGANISM: Artificial Sequence
<220> FEATURE:
<223> OTHER INFORMATION: Reverse primer for Deinococcus radiodurans BphP
      3-11 a.a.

<400> SEQUENCE: 17
gcgagctcga attctcacgg tggaaaaaag gcaacgg                                  38

<210> SEQ ID NO 18
<211> LENGTH: 38
<212> TYPE: DNA
<213> ORGANISM: Artificial Sequence
<220> FEATURE:
<223> OTHER INFORMATION: Forward primer for Deinococcus radiodurans BphP
      3-10 a.a.

<400> SEQUENCE: 18
gcctcgaggg atccatgcgg gacccgttgc ccttttttt                                38

<210> SEQ ID NO 19
<211> LENGTH: 38
<212> TYPE: DNA
<213> ORGANISM: Artificial Sequence
<220> FEATURE:
<223> OTHER INFORMATION: Reverse primer for Deinococcus radiodurans BphP
      3-10 a.a.

<400> SEQUENCE: 19
gcgagctcga attctcatgg aaaaaagggc aacgggtc                                 38

<210> SEQ ID NO 20
<211> LENGTH: 38
<212> TYPE: DNA
<213> ORGANISM: Artificial Sequence
<220> FEATURE:
<223> OTHER INFORMATION: Forward primer for Deinococcus radiodurans BphP
      4-12 a.a.

```
<400> SEQUENCE: 20
gcctcgaggg atccatggac ccgttgccct ttttttcca                    38

<210> SEQ ID NO 21
<211> LENGTH: 38
<212> TYPE: DNA
<213> ORGANISM: Artificial Sequence
<220> FEATURE:
<223> OTHER INFORMATION: Reverse primer for Deinococcus radiodurans BphP
      4-12 a.a.

<400> SEQUENCE: 21
gcgagctcga attctcaaag cggtggaaaa aagggcaa                     38

<210> SEQ ID NO 22
<211> LENGTH: 38
<212> TYPE: DNA
<213> ORGANISM: Artificial Sequence
<220> FEATURE:
<223> OTHER INFORMATION: Forward primer for 3rd Arg-substituted
      Deinococcus radiodurans BphP 3-11 a.a.

<400> SEQUENCE: 22
gcggatccat ggccgacccg ttgccctttt ttccaccg                     38

<210> SEQ ID NO 23
<211> LENGTH: 38
<212> TYPE: DNA
<213> ORGANISM: Artificial Sequence
<220> FEATURE:
<223> OTHER INFORMATION: Reverse primer for 3rd Arg-substituted
      Deinococcus radiodurans BphP 3-11 a.a.

<400> SEQUENCE: 23
gcgaattctc acggtggaaa aaagggcaac gggtcggc                     38

<210> SEQ ID NO 24
<211> LENGTH: 38
<212> TYPE: DNA
<213> ORGANISM: Artificial Sequence
<220> FEATURE:
<223> OTHER INFORMATION: Forward primer for 4th Asp-substituted
      Deinococcus radiodurans BphP 3-11 a.a.

<400> SEQUENCE: 24
gcggatccat gcgggccccg ttgccctttt ttccaccg                     38

<210> SEQ ID NO 25
<211> LENGTH: 38
<212> TYPE: DNA
<213> ORGANISM: Artificial Sequence
<220> FEATURE:
<223> OTHER INFORMATION: Reverse primer for 4th Asp-substittued
      Deinococcus radiodurans BphP 3-11 a.a.

<400> SEQUENCE: 25
gcgaattctc acggtggaaa aaagggcaac ggggcccg                     38

<210> SEQ ID NO 26
<211> LENGTH: 38
<212> TYPE: DNA
<213> ORGANISM: Artificial Sequence
<220> FEATURE:
<223> OTHER INFORMATION: Forward primer for 5th Pro-substituted
      Deinococcus radiodurans BphP 3-11 a.a.

<400> SEQUENCE: 26
```

-continued gcggatccat gcgggacgcc ttgccctttt ttccaccg        38

<210> SEQ ID NO 27
<211> LENGTH: 38
<212> TYPE: DNA
<213> ORGANISM: Artificial Sequence
<220> FEATURE:
<223> OTHER INFORMATION: Reverse primer for 5th Pro-substituted
      Deinococcus radiodurans BphP 3-11 a.a.

<400> SEQUENCE: 27
gcgaattctc acggtggaaa aaagggcaag gcgtcccg        38

<210> SEQ ID NO 28
<211> LENGTH: 38
<212> TYPE: DNA
<213> ORGANISM: Artificial Sequence
<220> FEATURE:
<223> OTHER INFORMATION: Forward primer for 6th Leu-substituted
      Deinococcus radiodurans BphP 3-11 a.a.

<400> SEQUENCE: 28
gcggatccat gcgggacccg gccccttttt ttccaccg        38

<210> SEQ ID NO 29
<211> LENGTH: 38
<212> TYPE: DNA
<213> ORGANISM: Artificial Sequence
<220> FEATURE:
<223> OTHER INFORMATION: Reverse primer for 6th Leu-substituted
      Deinococcus radiodurans BphP 3-11 a.a.

<400> SEQUENCE: 29
gcgaattctc acggtggaaa aaaggggggcc gggtcccg        38

<210> SEQ ID NO 30
<211> LENGTH: 38
<212> TYPE: DNA
<213> ORGANISM: Artificial Sequence
<220> FEATURE:
<223> OTHER INFORMATION: Forward primer for 7th Pro-substituted
      Deinococcus radiodurans BphP 3-11 a.a.

<400> SEQUENCE: 30
gcggatccat gcgggacccg ttggccttttt ttccaccg        38

<210> SEQ ID NO 31
<211> LENGTH: 38
<212> TYPE: DNA
<213> ORGANISM: Artificial Sequence
<220> FEATURE:
<223> OTHER INFORMATION: Reverse primer for 7th Pro-substituted
      Deinococcus radiodurans BphP 3-11 a.a.

<400> SEQUENCE: 31
gcgaattctc acggtggaaa aaaggccaac gggtcccg        38

<210> SEQ ID NO 32
<211> LENGTH: 38
<212> TYPE: DNA
<213> ORGANISM: Artificial Sequence
<220> FEATURE:
<223> OTHER INFORMATION: Forward primer for 8th Phe-substituted
      Deinococcus radiodurans BphP 3-11 a.a.

<400> SEQUENCE: 32
gcggatccat gcgggacccg ttgcccgcct ttccaccg                              38

<210> SEQ ID NO 33
<211> LENGTH: 38
<212> TYPE: DNA
<213> ORGANISM: Artificial Sequence
<220> FEATURE:
<223> OTHER INFORMATION: Reverse primer for 8th Phe-substituted
      Deinococcus radiodurans BphP 3-11 a.a.

<400> SEQUENCE: 33
gcgaattctc acggtggaaa ggcgggcaac gggtcccg                              38

<210> SEQ ID NO 34
<211> LENGTH: 38
<212> TYPE: DNA
<213> ORGANISM: Artificial Sequence
<220> FEATURE:
<223> OTHER INFORMATION: Forward primer for 9th Phe-substituted
      Deinococcus radiodurans BphP 3-11 a.a.

<400> SEQUENCE: 34
gcggatccat gcgggacccg ttgccctttg ccccaccg                              38

<210> SEQ ID NO 35
<211> LENGTH: 38
<212> TYPE: DNA
<213> ORGANISM: Artificial Sequence
<220> FEATURE:
<223> OTHER INFORMATION: Reverse primer for 9th Phe-substituted
      Deinococcus radiodurans BphP 3-11 a.a.

<400> SEQUENCE: 35
gcgaattctc acggtggggc aaagggcaac gggtcccg                              38

<210> SEQ ID NO 36
<211> LENGTH: 9
<212> TYPE: PRT
<213> ORGANISM: Artificial Sequence
<220> FEATURE:
<223> OTHER INFORMATION: 10th Pro-substituted Deinococcus radiodurans
      BphP 3-11 a.a.

<400> SEQUENCE: 36

Arg Asp Pro Leu Pro Phe Phe Ala Pro
1               5

<210> SEQ ID NO 37
<211> LENGTH: 38
<212> TYPE: DNA
<213> ORGANISM: Artificial Sequence
<220> FEATURE:
<223> OTHER INFORMATION: Forward primer for 10th Pro-substituted
      Deinococcus radiodurans BphP 3-11 a.a.

<400> SEQUENCE: 37
gcggatccat gcgggacccg ttgccctttt ttgccccg                              38

<210> SEQ ID NO 38
<211> LENGTH: 38
<212> TYPE: DNA
<213> ORGANISM: Artificial Sequence
<220> FEATURE:
<223> OTHER INFORMATION: Reverse primer for 10th Pro-substituted
      Deinococcus radiodurans BphP 3-11 a.a.

<400> SEQUENCE: 38
gcgaattctc acggggcaaa aaagggcaac gggtcccg         38

<210> SEQ ID NO 39
<211> LENGTH: 38
<212> TYPE: DNA
<213> ORGANISM: Artificial Sequence
<220> FEATURE:
<223> OTHER INFORMATION: Forward primer for 11th Pro-substituted
      Deinococcus radiodurans BphP 3-11 a.a.

<400> SEQUENCE: 39
gcggatccat gcgggacccg ttgccctttt ttccagcc         38

<210> SEQ ID NO 40
<211> LENGTH: 38
<212> TYPE: DNA
<213> ORGANISM: Artificial Sequence
<220> FEATURE:
<223> OTHER INFORMATION: Reverse primer for 11th Pro-substituted
      Deinococcus radiodurans BphP 3-11 a.a.

<400> SEQUENCE: 40
gcgaattctc aggctggaaa aaagggcaac gggtcccg         38

<210> SEQ ID NO 41
<211> LENGTH: 38
<212> TYPE: DNA
<213> ORGANISM: Artificial Sequence
<220> FEATURE:
<223> OTHER INFORMATION: Forward primer for Deinococcus radiodurans BphP
      3-11 a.a.

<400> SEQUENCE: 41
gcctcgaggg atccatgcgg gacccgttgc cctttttt         38

<210> SEQ ID NO 42
<211> LENGTH: 38
<212> TYPE: DNA
<213> ORGANISM: Artificial Sequence
<220> FEATURE:
<223> OTHER INFORMATION: Reverse primer for Deinococcus radiodurans BphP
      3-11 a.a.

<400> SEQUENCE: 42
gcgagctcga attctcacgg tggaaaaaag gcaacgg         38

<210> SEQ ID NO 43
<211> LENGTH: 41
<212> TYPE: DNA
<213> ORGANISM: Artificial Sequence
<220> FEATURE:
<223> OTHER INFORMATION: Forward primer for c-myc tag

<400> SEQUENCE: 43
gcggatccat ggaacaaaaa ttaatttctg aagaagattt a      41

<210> SEQ ID NO 44
<211> LENGTH: 41
<212> TYPE: DNA
<213> ORGANISM: Artificial Sequence
<220> FEATURE:
<223> OTHER INFORMATION: Reverse primer for c-myc tag

<400> SEQUENCE: 44
gcgaattctc ataaatcttc ttcagaaatt aattttttgtt c     41

```
<210> SEQ ID NO 45
<211> LENGTH: 720
<212> TYPE: DNA
<213> ORGANISM: Artificial Sequence
<220> FEATURE:
<223> OTHER INFORMATION: Nucleotides for Green Flourescent Protein

<400> SEQUENCE: 45
atggtgagca agggcgagga gctgttcacc ggggtggtgc ccatcctggt cgagctggac      60
ggcgacgtaa acggccacaa gttcagcgtg tccggcgagg gcgagggcga cgccacctac     120
ggcaagctga ccctgaagtt catctgcacc accggcaagc tgcccgtgcc ctggcccacc     180
ctcgtgacca ccttcagcta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actcacggca tggacgagct gtacaagtaa     720

<210> SEQ ID NO 46
<211> LENGTH: 56
<212> TYPE: DNA
<213> ORGANISM: Artificial Sequence
<220> FEATURE:
<223> OTHER INFORMATION: Forward primer for BRT tagged Green Fluorescent
      Protein

<400> SEQUENCE: 46
gcctcgagat gagggatcca cttccattct tccctccaat ggtgagcaag ggcgag          56

<210> SEQ ID NO 47
<211> LENGTH: 29
<212> TYPE: DNA
<213> ORGANISM: Artificial Sequence
<220> FEATURE:
<223> OTHER INFORMATION: Reverse primer for BRT tagged Green Fluorescent
      Protein

<400> SEQUENCE: 47
gcgagctctt acttgtacag ctcgtccat                                        29

<210> SEQ ID NO 48
<211> LENGTH: 66
<212> TYPE: DNA
<213> ORGANISM: Artificial Sequence
<220> FEATURE:
<223> OTHER INFORMATION: Forward primer for c -myc tagged Green
      Fluorescent Protein

<400> SEQUENCE: 48
ggagaggacc tcgagatgga acaaaagctt atttctgaag aagatcttat ggtgagcaag      60
ggcgag                                                                 66

<210> SEQ ID NO 49
<211> LENGTH: 29
<212> TYPE: DNA
<213> ORGANISM: Artificial Sequence
```

```
<220> FEATURE:
<223> OTHER INFORMATION: Reverse primer for c-myc tagged Green
      Fluorescent Protein

<400> SEQUENCE: 49
gcgagctctt acttgtacag ctcgtccat                                    29

<210> SEQ ID NO 50
<211> LENGTH: 29
<212> TYPE: DNA
<213> ORGANISM: Artificial Sequence
<220> FEATURE:
<223> OTHER INFORMATION: Forward primer for Deinococcus radiodurans BphP
      12-321 a.a.

<400> SEQUENCE: 50
ccatggcacc gctttacctt ggtggcccg                                    29

<210> SEQ ID NO 51
<211> LENGTH: 57
<212> TYPE: DNA
<213> ORGANISM: Artificial Sequence
<220> FEATURE:
<223> OTHER INFORMATION: Reverse primer for BRT tagged Deinococcus
      radiodurans BphP 12-321 a.a.

<400> SEQUENCE: 51
ctcgagtcac ggtggaaaaa agggcaacgg gtcccgcgct tccttgacct gaacttg     57

<210> SEQ ID NO 52
<211> LENGTH: 54
<212> TYPE: DNA
<213> ORGANISM: Artificial Sequence
<220> FEATURE:
<223> OTHER INFORMATION: Reverse primer for Flag tagged Deinococcus
      radiodurans BphP 12-321 a.a.

<400> SEQUENCE: 52
ctcgagtcac ttatcgtcgt catccttgta atccgcttcc ttgacctgaa cttg        54

<210> SEQ ID NO 53
<211> LENGTH: 48
<212> TYPE: DNA
<213> ORGANISM: Artificial Sequence
<220> FEATURE:
<223> OTHER INFORMATION: Reverse primer for His tagged Deinococcus
      radiodurans BphP 12-321 a.a.

<400> SEQUENCE: 53
ctcgagtcag tggtggtggt ggtggtgcgc ttccttgacc tgaacttg               48

<210> SEQ ID NO 54
<211> LENGTH: 60
<212> TYPE: DNA
<213> ORGANISM: Artificial Sequence
<220> FEATURE:
<223> OTHER INFORMATION: Reverse primer for c-myc tagged Deinococcus
      radiodurans BphP 12-321 a.a.

<400> SEQUENCE: 54
ctcgagtcat aaatcttctt cagaaattaa tttttgttcc gcttccttga cctgaacttg  60

<210> SEQ ID NO 55
<211> LENGTH: 6
<212> TYPE: PRT
<213> ORGANISM: Artificial Sequence
<220> FEATURE:
```

```
<223> OTHER INFORMATION: Linker

<400> SEQUENCE: 55

Gly Gly Ser Gly Gly Thr
1               5

<210> SEQ ID NO 56
<211> LENGTH: 5
<212> TYPE: PRT
<213> ORGANISM: Artificial Sequence
<220> FEATURE:
<223> OTHER INFORMATION: Linker

<400> SEQUENCE: 56

Gly Gly Gly Gly Ser
1               5

<210> SEQ ID NO 57
<211> LENGTH: 10
<212> TYPE: PRT
<213> ORGANISM: Artificial Sequence
<220> FEATURE:
<223> OTHER INFORMATION: Linker

<400> SEQUENCE: 57

Gly Gly Gly Gly Ser Gly Gly Gly Gly Ser
1               5                   10
```

PEPTIDE TAG AND USES THEREOF

CROSS-REFERENCE TO RELATED APPLICATIONS

This application is the United States national phase of International Application No. PCT/KR2013/005432 filed Jun. 20, 2013, and claims priority to Korean Patent Application Nos. 10-2012-0079615 and 10-2012-0124732, filed Jul. 20, 2012 and Nov. 6, 2012, respectively, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 150004_ST25.txt. The size of the text file is 27,685 bytes, and the text file was created on Feb. 20, 2015.

TECHNICAL FIELD

The present invention relates to an epitope tagging system for a detection or purification of target protein, and more particularly, novel peptide tags derived from bacteriophytochrome (BphP) that is photoreceptor protein of *Deinococcusradiodurans*, an antibody capable of specifically recognizing the peptide tags, and hybridoma cell lines capable of producing the antibody. In addition, the present invention relates to polynucleotide encoding the peptide tags, or vector or transformant including the polynucleotide encoding the peptide tags, fusion protein including the peptide tags, and a method or kit for producing, detecting, or purifying the fusion protein.

BACKGROUND ART

Useful protein or polypeptide may be produced by a synthesis or isolated from natural sources. However, these methods have disadvantages in that it is uneconomical in terms of cost and time and an output thereof is limited. Therefore, it is preferable that target protein and target polypeptide are produced through a culture of transformant prepared by a recombination in order for the target protein or target polypeptide to be over-expressed. However, polypeptide (especially, short polypeptide) produced under cell environment may be sensitive to a degradation due to a function of protease present in a cell, or since not all antibodies to all the target proteins are present, it may be difficult to purify the target proteins without the corresponding antibodies.

In order to overcome such a problem, a protein tagging or epitope tagging has been used. The protein tagging or epitope tagging is a recombinant DNA method, which includes preparing a recombinant nucleic acid molecule prepared by ligating a coding sequence of epitope tag to a coding sequence of target protein and expressing the recombinant nucleic acid molecule in a proper host cell, and is used for detecting, quantifying, or purifying the target protein using an antibody to the epitope tag, or determining a location of the target protein in a cell, confirming functionality, and the like. Many epitope tags and antibodies that are ligands of the epitope tags are commercially available, and in the case of selecting suitable epitope tags and antibodies thereof, target proteins can be detected or purified by using Western blot analysis, immunoprecipitation, immunofluorescence, immunocytochemistry, immunoaffinity purification, and the like. Therefore, it is unnecessary to produce the antibody to the target protein.

Recently, as an epitope tag used for a protein tagging or epitope tagging, it is possible to use many unique tags such as short peptide tag having about 6 amino acid residues (for example, 6×His tag) or large protein having about 40 kDa (for example, MBP) [see Stevens, R. C., (2000) Structure Fold Des 8:R177-85]. Generally, peptide tag composed of 3 to 30 amino acids is used. His-tagged protein is specifically trapped on a Ni-NTA (nickel-nitrilotriacetic acid) resin, and may be eluted by using EDTA or imidazole. In addition, maltose-binding protein (MBP, 396 amino acids, 40 kDa), staphylococcus protein A, calmodulin-binding peptide (CBP, 26 amino acids, 2.96 kDa), GFP (238 amino acids, 27 kDa), and glutathione-S-transferase (GST, 211 amino acids, 26 kDa) may be used for detecting or purifying procaryotic proteins and eukaryotic proteins. Furthermore, epitope tag that is generally most often used may include a c-myc tag, a HA tag, a FLAG tag, and the like. The c-myc tag is an epitope tag having 10 amino acids length derived from human c-myc protein [Evans et al., (1985) Mol. Cell. Biol., 12:3610-3616], and the HA tag is an epitope tag having 9 amino acids length derived from influenza hamagglutinin HA-1 protein [Field et al., (1988) Mol. Cell. Biol., 8: 2159-2165]. The FLAG tag is an epitope tag having 8 amino acids length derived from a bacteriophage T7 [Hopp et al., (1988) Bio/Technology, 6:1204-1210].

Meanwhile, it is preferable that an epitope tag used for tagging an epitope minimally influence on a three-dimensional structure and biological activity of target protein when fusing with the target protein. However, a long epitope tag (for example, a GST tag or a MBP tag) has generally a problem in that it allows functions of the target protein to be changed. On the other hand, epitope tags having a relatively short length, for example, a FLAG tag, a c-myc tag, and the like scarcely influence on properties of target protein fused therewith, can be very specifically bound to antibodies therefor, and do not have to be removed from the fusion proteins on some occasions. Thus, they are mostly used now. However, there are problems in that since the amino acid sequences of c-myc tag and FLAG tag are included in many proteins among the proteins in cells of organisms that are known up to now, non-specific reactions of antibodies recognizing the tags are induced and interrupt an isolation and confirmation of specific target proteins, resulting in decreasing reliability of the experiments [Ksenija Gasic et al., (2005) Plant molecular biology reporter 23:9-16]. In order to overcome the non-specific reaction problem, an affinity purification system has been developed, in which for such an affinity purification system, two different tags are sequentially fused to N-terminal of protein, and then used [Rigaut, G., et al. (1999) Nat Biotechnol 17:1030-2].

Accordingly, it is needed to develop novel peptide tags capable of removing non-specific reaction that is a problem in the conventional epitope tagging system for detecting and purifying a fusion protein expressed in a recombinant host cell using an epitope tag and antibody thereto, and having short amino acid sequence at the same time, and an antibody capable of being used in pairs with the novel peptide tags.

DISCLOSURE OF INVENTION

Technical Problem

An object of the present invention is to provide novel peptide tags that are useful for detecting or purifying target proteins, and uses thereof.

Another object of the present invention is to provide a novel antibody capable of specifically recognizing the novel epitope tag or selectively binding the novel epitope tag, hybridoma cell lines capable of producing the antibody, and uses thereof.

Solution to Problem

The inventors of the present invention conducted a thorough investigation with regard to the development of a peptide tag and antibody thereto that are useful for detecting or purifying target protein, and as a result, the inventors found that hybridoma producing a monoclonal antibody was obtained by using a bacteriophytochrome (BphP) that is photoreceptor protein of *Deinococcusradiodurans*, heterotrophic bacteria, or a fragment thereof as an immunogen, and then with the produced antibody, an epitope mapping was performed to a bacteriophytochrome (BphP) of *Deinococcus radiodurans* as an object, resulting in finding an epitope composed of 9 amino acids. Thus, the inventors finally completed the present invention.

In order to achieve such an object, the present invention provides a peptide tag including peptide having an amino acid sequence as set forth in SEQ ID NO: 1 or peptide having an amino acid sequence as set forth in SEQ ID NO: 2 as a recognition site of antibody or a binding site of antibody. In addition, the present invention provides polynucleotide encoding the peptide tag. At this time, the polynucleotide encoding the peptide tag may include preferably a base sequence as set forth in SEQ ID NO: 7 or a base sequence as set forth in SEQ ID NO: 8. In addition, the polynucleotide encoding the peptide tag may be synthesized by a pair of primers that are composed of a forward primer having a base sequence as set forth in SEQ ID NO: 16 and a reverse primer having a base sequence as set forth in SEQ ID NO: 17 or a pair of primers that are composed of a forward primer having a base sequence as set forth in SEQ ID NO: 32 and a reverse primer having a base sequence as set forth in SEQ ID NO: 33. In addition, the present invention includes a recombinant vector including polynucleotide encoding the peptide tag. At this time, the recombinant vector may be a cloning vector or expression vector. In addition, preferably, the expression vector may further include target polynucleotide encoding target protein, and the target polynucleotide is ligated to the polynucleotide encoding the peptide tag. Furthermore, the present invention includes fusion protein including target protein and peptide tag that is bound thereto. At this time, the peptide tag constituting the fusion protein includes peptide having an amino acid sequence as set forth in SEQ ID NO: 1 or peptide having an amino acid sequence as set forth in SEQ ID NO: 2 as a recognition site of antibody or a binding site of antibody. In addition, the present invention provides polynucleotide encoding the fusion protein. Furthermore, the present invention provides transformant that is introduced with any one selected from the group consisting of polynucleotide encoding the peptide tag, a recombinant vector including polynucleotide encoding the peptide tag, polynucloetide encoding the fusion protein, and a recombinant vector including the polynucleotide encoding the fusion protein. In addition, the present invention provides a method of detecting fusion protein, in which the method includes binding the fusion protein and antibody to a peptide tag through contacting each other; and determining a presence of the fusion protein bound to the antibody or analyzing the amount thereof. At this time, the fusion protein may be expressed by transformant including polynucleotide encoding the fusion protein or a recombinant vector including the fusion protein. Further, the antibody is preferably a monoclonal antibody produced by a hybridoma cell line having a deposition number of KCTC 12283BP. Furthermore, the present invention provides a method of purifying the fusion protein, in which the method includes binding the fusion protein and antibody to the peptide tag through contacting each other; and collecting the fusion protein bound to the antibody. At this time, the fusion protein may be expressed by transformant including polynucleotide encoding the fusion protein or a recombinant vector including the fusion protein. In addition, the antibody is preferably a monoclonal antibody produced by a hybridoma cell line having a deposition number of KCTC 12283BP. Furthermore, the present invention provides a kit for detecting or purifying fusion protein, including any one selected from the group consisting of polynucleotide encoding the peptide tag, a pair of primers for synthesizing the polynuleotide encoding the peptide tag, a recombinant vector including the polynucleotide encoding the peptide tag, polynucleotide encoding the fusion protein, and a recombinant vector including the polynucleotide encoding the fusion protein; and any one selected from the group consisting of an antibody that is specifically bound to the peptide having an amino acid sequence as set forth in SEQ ID NO: 1 or peptide having an amino acid sequence as set forth in SEQ ID NO: 2, or hybridoma cell lines producing the antibody. At this time, the antibody is preferably a monoclonal antibody produced by a hybridoma cell line having a deposition number of KCTC 12283BP.

In order to achieve another object, the present invention provides an antibody to peptide having an amino acid sequence as set forth in SEQ ID NO: 1 or peptide having an amino acid sequence as set forth in SEQ ID NO: 2. At this time, the antibody is preferably a monoclonal antibody. In addition, the monoclonal antibody is IgG 2a that is a heavy chain isotype or K (kappa) that is a light chain isotype. In addition, the present invention provides a hybridoma cell line producing the antibody. At this time, the hybridoma cell line has a deposition number of KCTC 12283BP. Furthermore, the present invention provides a kit including the antibody or the hybridoma cell line. At this time, the antibody is fixed to a support. In addition, preferably, the kit may further include a means of detecting the antibody (antibody to peptide having an amino acid sequence as set forth in SEQ ID NO: 1 or peptide having an amino acid sequence as set forth in SEQ ID NO: 2). The detection means is preferably a secondary antibody capable of being bound to the antibody to peptide having an amino acid sequence as set forth in SEQ ID NO: 1 or peptide having an amino acid sequence as set forth in SEQ ID NO: 2. In addition, the secondary antibody may be preferably conjugated with a marker selected from the group consisting of enzyme, a radioactive substance or a fluorescent material. In addition, the kit may be used for detecting or purifying target protein, and the fusion protein including peptide having an amino acid sequence as set forth in SEQ ID NO: 1 or peptide having an amino acid sequence as set forth in SEQ ID NO: 2 that is bound to the target protein.

Advantageous Effects of Invention

The novel peptide tag according to the present invention has advantages in that it has a short length and can remove a non-specific reaction of the conventional c-myc tag and FLAG tag. Therefore, in the case of using the novel peptide tag according to the present invention and antibody thereto, the fusion protein expressed in a recombinant cell can be very effectively detected or purified. In addition, an epitope tagging system including the novel peptide tag according to the present invention and antibody thereto can be applied in various fields such as a determination of a site, a confirmation of functionality, detection, and purification of specific protein in a cell, and researches on interaction between proteins.

BRIEF DESCRIPTION OF DRAWINGS

In FIG. 1, (A) shows a mimetic diagram schematically exhibiting a gene construct used for expressing BphP protein and BphN protein of *Deincoccusradiodurans*. FL, Whole length (1 to 755 amino acids, BphP); APHY/HKD (1 to 321 amino acids, BphN); in FIG. 1, (B) shows a result (right) obtained by purifying BphP apoprotein and BphN apoprotein of *Deinococcus radiodurans* using a Ni$^+$-NTA affinity chromatography, culturing the purified apoproteins with BV for 20 minutes, subjecting the resulting apoproteins to a SDS-PAGE, and then detecting a BV binding by a zinc-inducing fluorescence and a result (left) obtained by staining it with a Coomassie Blue. 1: a BphP crude extract, 2: a purified BphP, 3: a BphN crude extract, 4: a purified BphN. Purification conditions×binding & washing: pH 8.0, 100 mM Tris, 200 mM NaCl, 10 mM imidazole/elution: pH 8.0, 100 mM Tris, 200 mM NaCl, 150 mM imidazole;

In FIG. 4, "a-GST" represents an anti-GST antibody;

In FIG. 6, "a-myc" represents an anti-myc antibody and "a-GST" represents an anti-GST antibody;

In FIG. 7, a "myc" represents an anti-myc antibody;

Mode for the Invention

Figure 1:
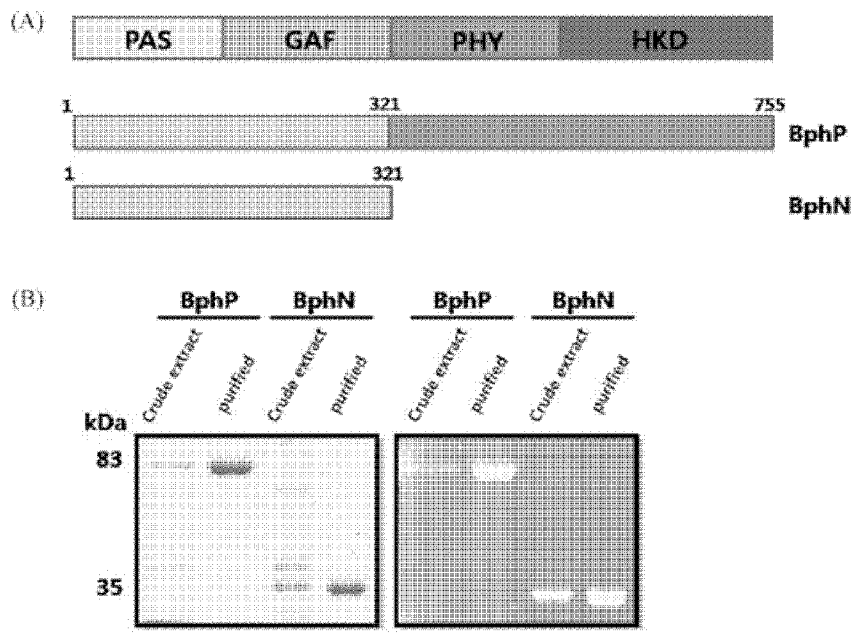
FIG. 1 shows a diagram illustrating a purification result of DrBphP and DrBphN using a His tag column chromatography.

According to an aspect of the present invention, there is provided a novel peptide tag capable of being used for an epitope tagging system for purifying or detecting target protein. The novel peptide tag according to the present invention includes peptide having an amino acid sequence as set forth in SEQ ID NO: 1 or peptide having an amino acid sequence as set forth in SEQ ID NO: 2 as a recognition site of an antibody or binding site of an antibody. For the specification of the present invention, the peptide tag and a protein tag or epitope tag may be interchangeably used. The term "peptide tag" in the present invention means peptide that is fused to target protein and then is capable of being used as a tag. In addition, the term "epitope" in the present invention means a antigen-binding site that is recognized by a specific antibody or a certain site of an antigen that is reacted with B cell or T cell. When the peptide tag according to the present invention includes peptide having an amino acid sequence as set forth in SEQ ID NO: 1 or peptide having an amino acid sequence as set forth in SEQ ID NO: 2 as a recognition site of an antibody or binding site of an antibody, the length is not greatly limited. For example, the peptide tag according to the present invention may be preferably peptide having 9 to 30 amino acids in consideration of the number of amino acid residues of an epitope tag that is generally used, and more preferably, peptide having an amino acid sequence as set forth in SEQ ID NO: 1 or peptide having an amino acid sequence as set forth in SEQ ID NO: 2. The peptide having an amino acid sequence as set forth in SEQ ID NO: 1 or peptide having an amino acid sequence as set forth in SEQ ID NO: 2 is derived from a bacteriophytochrome (BphP) that is photoreceptor protein of *Deinococcus radiodurans*. Specifically, the peptide having an amino acid sequence as set forth in SEQ ID NO: 1 is peptide having amino acid residues that are located at third to eleventh locations based on N-terminal among the full amino acid sequences (SEQ ID NO: 3) of the Bacteriophytochrome (BphP) that is photoreceptor protein of *Deinococcus radiodurans*. In addition, the peptide having an amino acid sequence as set forth in SEQ ID NO: 2 is peptide having amino acid residues that are located at third to eleventh locations based on N-terminal among the full amino acid sequences (SEQ ID NO: 3) of the Bacteriophytochrome (BphP) that is photoreceptor protein of *Deinococcus radiodurans*, in which phenylalanine, an amino acid residue located at the eighth location is substituted with alanine.

According to an aspect of the present invention, the peptide tag having an amino acid sequence as set forth in SEQ ID NO: 1 or the peptide tag having an amino acid sequence as set forth in SEQ ID NO: 2 were determined by selecting hybridoma cell lines through a general method using a bacteriophytochrome of *Deinococcus radiodurans* as an immunogen; obtaining the purified antibody from the hybridoma cell lines, and then performing an epitope mapping using the antibody. Hereinafter, the bacteriophytochrome of *Deinococcus radiodurans* will be referred to as "DrBphP" or "BphP". *Deinococcus radiodurans* is a kind of extremophiles capable of being grown even under an extremely low temperature, drying, low oxygen, and strong acid environment. Phytochrome is photoreceptor protein capable of absorbing external light signals and delivering the signals to a lower part, and according to the conventional theory, it was known that the phytochrome is present in higher plants, but in the recent year, various phytochrome-like photoreceptors were discovered in cyanobacteria, proteobacteria, actinobacteria, fungi, and the like. Especially, phytochrome-like photoreceptors found in *Deinococcus radiodurans*, *Pseudomonas aeruginosa*, and the like are called BphP, and among them, DrBphP is consisted of 755 amino acids marked as amino acid sequence as set forth in SEQ ID NO: 3 [Davis S J, et al., (1999) Science 286, 2517-2520]. A N-terminal region of the BphP is constituted of the similar structure to a plant phytochrome, but a C-terminal region has histidine kinase domain (HKD) that is different from the plant phytochrome [Karniol R, et al., (2005) Photosynth Res 392, 103-116; Giraud E et al., (2008) Photosynth Res 97, 141-153]. In addition, the DrBphP binds with biliverdine (BV) without any help of other factors and thus forms a reversible Pr/Pfr isoform [Vierstra R D et al., (2000) Semin Cell Dev Biol 11, 511-521; Bhoo S H, et al., (2001) Nature 414, 776-779; Rockwell N.C., et al., (2006) Annu Rev Plant Biol 57, 837-858].

Figure 2:
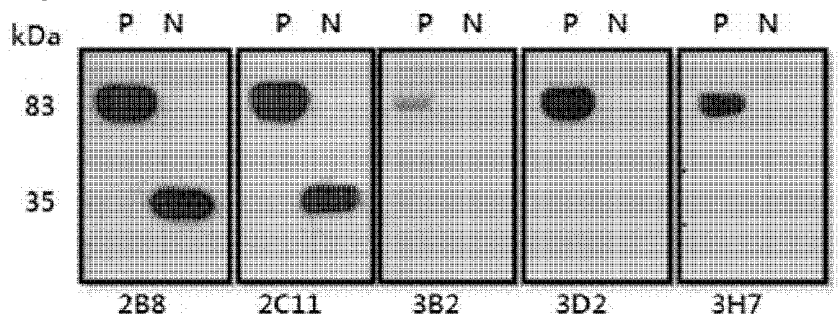
FIG. 2 shows a diagram illustrating a result of a western blotting performed by using purified BphP and BphN with a selected monoclonal antibody. Purified BphP and BphN were subjected to a SDS-PAGE and purified monoclonal antibodies (2B8, 2C11, 3B2, 3D2, 3H7) of BphP were subjected to a western blotting. P; BphP, N; BphN. It was confirmed by using a western blotting that the 2B8 antibody among the monoclonal antibodies recognized an epitope present at N-terminal of the BphP protein.
Figure 3:
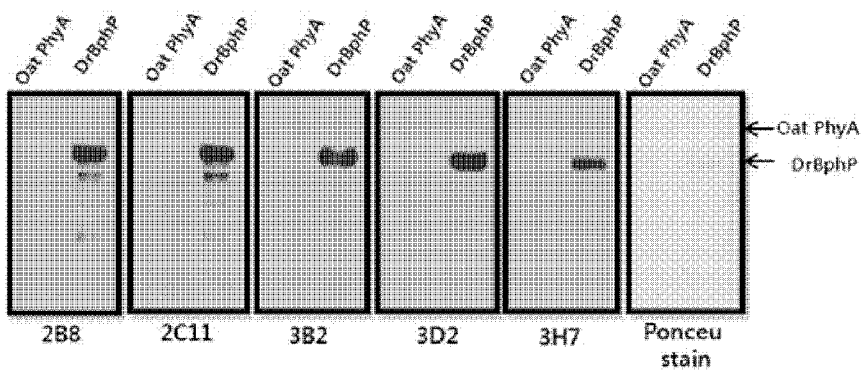
FIG. 3 shows a result of confirming whether or not Oat PhyA that is oat phytochrome protein having a PCD structure constituting a N-terminal region that is similar to DrBphP was reacted with five monoclonal antibodies of BphP.

Hereinafter, a step of an epitope mapping for determining the novel peptide tag according to the present invention will be described in detail. First, a gene (SEQ ID NO: 4) corresponding to the whole length of BphP of *Deinococcus radiodurans* and a gene (SEQ ID NO: 5) corresponding to polypeptide (SEQ ID NO: 6; hereinafter, referred to as "BphN" or "DrBphN") constituted of amino acids located at 1 to 321 locations based on N-terminal of DrBphP were constructed [see (A) in FIG. 1]; the gene constructs were inserted into pET28a(+) vector; and then the gene constructs inserted into the vector were expressed by using a BL21 competent cell. Then, proteins were purified by using a $Ni^+$-NTA affinity chromatography using a His tag included in the pET28a(+) vector. Since the expressed BphP protein (SEQ ID NO: 3) and BphN protein (SEQ ID NO: 6) includes all of Cys-24 residues, and PAS and GAF domains playing on an important role for a BV binding, only the proteins themselves can be bound to the BV. In order to confirm the expressions and purifications of BphP protein and BphN protein, the BV was added to the purified BphP protein and BphN protein, isothermal-treated at room temperature for 10 minutes, subjected to a SDS-PAGE, and then subjected to a coomassie staining and zinc blotting. As a result, it was confirmed that the BphP protein and BphN protein were expressed and purified [see (B) in FIG. 1]. Next, in order to prepare a monoclonal antibody to BphP, a BphP protein or BphN protein of *Deinococcus radiodurans* as an antigen along with a Complete Freund's adjuvant was intraperitoneally injected to the abdominal cavity of 6-week female BALB/c mouse, and then the mouse was sacrificed to obtain a B lymphocyte. Then, the B lymphocyte and myeloma cell were mixed, fused, and then cultured. Since then, while HAT medium and HT medium were exchanged, an antibody production of fusion cell was confirmed by an ELISA and then total 24 hybridoma cell line candidate clones were selected. The total 24 hybridoma cell line candidate clones were subjected to a fusion plate ELISA test using the BphP protein and BphN protein that were injected as an antigen, and then a degree of binding was confirmed (Table 3). As a result, it was estimated that since a 2B 8 clone and 2C 11 clone were colored in a high level in all the BphP protein and BphN protein of *Deinococcus radiodurans*, the clones recognized the N-terminal site of the BphP protein. However, a 3B2 clone and 3D2 clone exhibited a high level in the BphP protein and almost 0 in the BphN protein, so that it was estimated that the clones recognized C-terminal site of the BphP protein. Unlike these clones, a 3H7 clone exhibited a high level in the BphP protein and also a predetermined level in the BphN protein, so that it was estimated that the clone recognized N-terminal site in some degree in addition to C-terminal site of the BphP protein. Since then, the five hybridoma cell line clones were subjected to a primary cloning plate ELISA test and then a secondary cloning plate ELISA test, and finally ascites was generated and then the antibodies were purified. As a result, five monoclonal antibodies, that is, a 2B8 antibody, 2C11 antibody, 3B2 antibody, 3D2 antibody, and 3H7 antibody were achieved. Since then, in order to confirm whether or not the same results were obtained to the pre-expressed and purified BphP protein and BphN protein, the purified antibodies were subjected to a western blotting. The respective monoclonal antibodies in a ratio of 1:1000 with respect to 2% skim milk as a primary antibody were used and then HRP-mouse antibody (SIGMA) was treated in a ratio of 1:10000 to 5 μg of the purified BphP protein and BphN protein, and then a western blotting was performed. As a result, all the 2B8 antibody and 2C11 antibody were bound to the BphP protein and BphN protein like the ELISA test to the hybridoma cell line clones (FIG. 2). Thus, it can be considered that the above two antibodies are bound to the N-terminal region of the BphP protein. In addition, bands of the 3B2 antibody and 3D2 antibody were appeared to the BphP protein, but not appeared to the BphN protein, so that it could be confirmed that the antibodies were bound to the C-terminal region of the BphP protein. However, the 3H7 antibody recognized only the BphP protein unlike the result of ELISA test. In addition, according to the binding degrees of the respective antibodies, the 2B8 antibody and 2C11 antibody binding to the N-terminal site were most strongly bound and the 3D2 antibody recognizing the C-terminal site expressed a weak band. As the next strong band, the strong binding band was expressed in order of the 3H7 antibody and 3B2 antibody. Meanwhile, the DrBphP has the similar structure as a plant phytochrome, and especially, PCD constituting the N-terminal site includes PAS, GAF, and PHY domains in all the DrBphP and plant phytochrome. It was confirmed whether or not these antibodies were reacted with oat phytochrome protein similar to the DrBphP. However, as a result, all the five monoclonal antibodies to the BphP protein of *Deinococcus radiodurans* were not bound to the oat phytochrome proteins (Oat PhyA) (FIG. 3). Accordingly, it was confirmed that the monoclonal antibodies to the BphP protein of *Deinococcus radiodurans* recognized the epitope different from the antibodies to the conventional oat phytochrome protein, so that they are new antibodies specific to the BphP. In addition, the present inventor found that by isolating the epitope recognized by the above antibodies, it was confirmed that the epitope can be used as a specific peptide tag that was not included in any other proteins of the organisms that were conventionally known. Specifically, in order to confirm the epitope of 2B8 antibody that was most strongly bound among the monoclonal antibodies to the BphP protein of *Deinococcusradiodurans*, a DrBphP recombinant partial peptide was prepared, and an epitope mapping was performed. The peptide fragments including each of the amino acid sequence (SEQ ID NO: 13) of 3 to 12 positions, the amino acid sequence (SEQ ID NO: 1) of 3 to 11 locations, the amino acid sequence of 3 to 10 locations and the amino acid sequence of 4 to 12 locations based on N-terminal among the total amino acid sequence (SEQ ID NO: 3) of DrBphP were prepared, and whether or not the peptide fragments were bound was confirmed by a western blotting. As a result, it was confirmed that the 2B8 antibody could accurately recognize the 9 amino acid and be bound to the 9 amino acids when having 9 amino acids (SEQ ID NO: 1) located at 3 to 11 locations based on N-terminal among the total amino acid sequence (SEQ ID NO: 3) of DrBphP was present. From the above result, it was confirmed that the epitope of 2B8 antibody was peptide having amino acid sequence as set forth in SEQ ID NO: 1, and the peptide could be used as a peptide tag. In addition, the peptide fragments, in which one amino acid residue of the amino acid sequence as set forth in SEQ ID NO: 1 was substituted with alanine, were prepared respectively, and then an epitope mapping was performed by using the 2B8 antibody. As a result, it was confirmed that the peptide having an amino acid sequence as set forth in SEQ ID NO: 2 could be used as another epitope of the 2B8 antibody.

In addition, the peptide tag of the present invention may be provided in a type of binding to other epitope tags that are known in order to secure various functionalities in addition to an amino acid sequence as set forth in SEQ ID NO: 1 or an amino acid sequence as set forth in SEQ ID NO: 2. For example, the peptide tag of the present invention may be provided in a type of double tags, in which a HA tag, FLAG tag, His tag, BCCP (biotin carboxyl carrier protein) or MBP (maltose binding protein) is bound to the amino acid sequence as set forth in SEQ ID NO: 1 or amino acid sequence as set forth in SEQ ID NO: 2, in order to improve detection ability, purification ability, availability of target protein, and the like (see U.S. Pat. No. 8,999,897, U.S. 20060099710, and U.S. Pat. No. 6,462,254). In addition, the peptide tag of the present invention may be provided in a type of triple tag or multiple tag, in which at least two tags selected from a HA tag, 6×His tags, c-myc tag, and V5 tag are bound to the amino acid sequence as set forth in SEQ ID NO: 1 or amino acid sequence as set forth in SEQ ID NO: 2 (see U.S. Pat. No. 8,546,307). In addition, the peptide tag of the present invention may be provided, like 3×FLAG tags, in a type of repeating the amino acid sequence as set forth in SEQ ID NO: 1 or amino acid sequence as set forth in SEQ ID NO: 2, or a type of substituting and deleting partial amino acid residues among the repeated amino acid sequences (see U.S. Pat. No. 7,135,624).

In a case where the peptide tag according to the present invention includes the amino acid sequence as set forth in SEQ ID NO: 1 or amino acid sequence as set forth in SEQ ID NO: 2, the corresponding antibody thereto can be used. For example, the above described 2B8 antibody is an antibody to the peptide tag including the amino acid sequence as set forth in SEQ ID NO: 1 or amino acid sequence as set forth in SEQ ID NO: 2. Meanwhile, mutants, and the like, in which partial amino acids constituting the amino acid sequence as set forth in SEQ ID NO: 1 or amino acid sequence as set forth in SEQ ID NO: 2 are individually substituted, deleted, added or modified, and at the same time has a predetermined level of binding activity to the 2B8 antibody, for example, at least 75% based on the original binding activity, may be included in a range of equivalents of the peptide tag according to the present invention. The substitution of amino acid may be preferably performed by a conservative amino acid replacement without a change of peptide properties. In addition, the modification of amino acid may be performed by glycosylation, acetylation, phosphorylation, and the like. Furthermore, the peptide tag according to the present invention may include a marked amino acid. Further, the peptide tag according to the present invention may include a peptide having increased structural stability to heat, pH, and the like and increased activity to an antibody by a mutation or modification of amino acid sequence. For example, a mutant tag of the peptide tag according to the present invention may include a peptide having an amino acid sequence as set forth in SEQ ID NO: 13 or a peptide having an amino acid sequence as set forth in SEQ ID NO: 36 as a recognition site of an antibody or binding site of antibody. The peptide having the amino acid sequence as set forth in SEQ ID NO: 13 is the peptide having amino acid residues located at third to twelfth locations based on N-terminal among the total amino acid sequence (SEQ ID NO: 3) of bacteriophytochrome (BphP) that is phoreceptor protein of Deinococcus radiodurans. In addition, the peptide having the amino acid sequence as set forth in SEQ ID NO: 36 is the peptide having amino acid residues located at third to eleventh locations based on N-terminal among the total amino acid sequence (SEQ ID NO: 3) of bacteriophytochrome (BphP) that is photoreceptor protein of Deinococcusradiodurans, in which proline, an amino acid residue located at tenth location among the amino acid residues located at the third to eleventh locations is substituted with alanine.

Another aspect of the present invention relates to polynucleotide encoding the above mentioned novel peptide tag, and a recombinant vector including the polynucleotide. In the present invention, the term "polynucleotide" means all non-modified or modified polyribonucleotide (RNA) or polydeoxyribonucleotide (DNA). The polynucleotide includes a hybrid molecule including DNA and RNA that may be single-strand or double-strand DNA, DNA that is a mixture of single-strand and double-strand region, single-strand or double-strand RNA, RNA that is a mixture of single-strand and double-strand region, and a mixture of single-strand or double-strand, or single-strand and double-strand regions, but the present invention is not limited thereto. In addition, the polynucleotide of the present invention includes a pair of primers used for synthesizing the above mentioned novel peptide tag as single-strand RNA or DNA. In addition, the polynucleotide of the present invention may be interchangeably used with nucleic acid molecules or oligonucleotide.

The polynucleotide encoding the peptide may include a non-translated sequence (for example, intron) or may not include a non-translated sequence (for example, cDNA). Information encoding peptide is specified by using codon. Typically, an amino acid sequence is encoded by polynucleotide using a universal gene code. "Codon" represents triplet of nucleotide determining an amino acid sequence in a polypeptide chain. Most organisms use 20 or 21 amino acids for preparing their polypeptides that are protein or protein precursor. Since adenine (A), guanine (G), cytosine (C) and thymine (T) that are four possible nucleotides are present in DNA, there are 64 possible triplets capable of encoding 20 amino acids and terminal signals. Due to such duplication, most amino acids are encoded by at least one triplet. Accordingly, the amino acids do not influence on an amino acid sequence of polypeptide to be encoded, and can allow a change of nucleotide sequence, in which the change refers to as "silent mutations" due to "codon degeneracy." All the silent mutations of polynucleotide encoding the novel peptide tag of the present invention are within the range of the present invention. Meanwhile, the codon specifying a single amino acid may not be used in a same frequency, and each of the organisms often represents a specific "codon-bias" to one of several codons encoding the same given amino acid. In a case where a coding region includes various rare codons or clusters of rare codons, a level of expression can be increased by removing a rare codon using a re-synthesis or mutation induction of gene [see J. Sambrook and D. W. Russell, Molecular Cloning: A Laboratory Manual, Third Edition, Cold Spring Harbor Press, Cold Spring Harbor, N.Y. (2001), at 15.12]. Thus, "codon selection" may be used for an optimization of expression in a selected host. The most preferable codon is a codon that is mostly found in high-level expressed gene. "Codon usage" in E. coli can be seen in Konigsberg, etal., Proc. Nat'l. Acad. Sci. U.S.A. 80:687-91 (1983).

In the case of chemically synthesizing and preparing a nucleotide sequence, a synthesis method that is widely known in the art, for example, the method that is disclosed in a document (Engels and Uhlmann, Angew Chem IntEd Engl., 37:73-127, 1988) can be used, and examples of the method may include a triester, phosphite, phosphoramidite and H-phosphate method, a PCR and other autoprimer methods, a oligonucleotide synthesis method on a solid support.

Therefore, the polynucleotide encoding the novel peptide tag of the present invention may be composed of various base sequences, and for example, the polynucleotide encoding the peptide tag having an amino acid sequence as set forth in SEQ ID NO: 1 may be preferably composed of a base sequence as set forth in 7 and the polynucleotide encoding the peptide tag having an amino acid sequence as set forth in SEQ ID NO: 2 may be preferably composed of a base sequence as set forth in SEQ ID NO: 8. In addition, a pair of primers for synthesizing polynucleotide encoding the peptide tag of the present invention may be composed of a forward primer having a base sequence as set forth in SEQ ID NO: 16 and a reverse primer having a base sequence as set forth in SEQ ID NO: 17 or also may be composed of a forward primer having a base sequence as set forth in SEQ ID NO: 32 and a reverse primer having a base sequence as set forth in SEQ ID NO: 33.

In addition, the present invention provides a recombinant vector including polynucleotide encoding the novel peptide tag. For example, the recombinant vector according to the present invention may include polynucleotide having a base sequence as set forth in SEQ ID NO: 7 or polynucleotide having a base sequence as set forth in SEQ ID NO: 8. The recombinant vector may be provided in a type of inserting the polynucleotide encoding the novel peptide tag into a cloning vector or expression vector using the known standard method. In the present invention, the term "vector" refers to as any vehicle for a cloning and/or transposition of base into a host cell. In the present invention, the vector may be a replicon capable of inducing replication of a foreign DNA fragment. The "replicon" refers to as any gene unit (for example, plasmid, phage, cosmid, chromosome, and virus) capable of functioning as an autounit of DNA replication invivo, that is, being replicated by a control itself. The term "vector" includes virus and non-virus vehicle for introducing a base into a host cell in vivo, invitro, or exvivo. The term "vector" may also include a miniglobular shape DNA. For example, the vector may be a plasmid without a bacteria DNA sequence. A removal of bacteria DNA sequence that is rich in CpG region is performed in order to decrease a transgene expression silencing and express more continuously from a plasmid DNA vector. In addition, the term "vector" may include a transposon [Izsvak etal. J. Mol. Biol. 302:93-102 (2000)] like a sleepling beauty or artificial chromosome. In the present invention, the term "cloning vector" is defined as a material capable of delivering a DNA fragment into a host cell and reproducing the DNA fragment. In the present invention, the cloning vector may further include polyadenylation signal, transcription termination sequence, and multiple cloning sites. At this time, the multiple cloning sites includes at least one endonuclease restriction site. In addition, the cloning vector may further include promoter. As an example, the polynucleotide encoding the novel peptide tag in the present invention may be located at upstream of polyadenylation signal and transcription termination sequence, and at least one endonuclease restriction site may be located at upstream of polyadenylation signal and transcription termination sequence. In addition, the term "expression vector" in the present invention is defined as a DNA sequence needed for transcription and translation of DNA cloned in a proper host. In addition, the term "expression vector" in the present invention means a gene construct including an essential control element that is operably linked to an insert to be expressed in the case of presenting in a cell of an object. The expression vector may be prepared and purified by using a standard recombinant DNA technique. A kind of the expression vector is not specifically limited as long as a desired gene can be expressed in various host cells of procaryotic and eukaryotic cells and the vector can have a function of producing a desired protein. However, it is preferable to use the vector having strong expression force and promotor having strong activity, and capable of producing foreign protein having the similar type as a natural state in quantity. The expression vector preferably includes at least, promoter, start codon, genes encoding the desired proteins, and stop codon terminator. In addition, the expression vector may properly include DNA encoding a signal peptide, a further expression control sequence, non-translated regions of 5'-side and 3'-side of the desired gene, a selection marker region, or a replicable unit. The "promoter" means a minimum sequence enough to direct translation. In addition, it may include a promoter construct enough to express promoter-dependent gene that can be controlled and induced by external signal or formulation or specific to a cell type. The promoter construct may be located at 5' or 3' site of the gene. The expression vector according to the present invention may include both the conservative promoter and inducible promoter. The promoter sequence may be derived from prokaryote, eukaryote, or virus. The term "operably linked" means that one function is controlled by other functions through a sequence correlation of polynucleotide on the single polynucleotide. For example, in a case where the promoter can control an expression of encoding sequence (that is, the encoding sequence is under a transcription control of the promoter), the promoter is linked to the coding sequence and then operated, or when the ribosome binding site may be located to promote translation, the ribosome binding site is linked to the encoding sequence and then operated. The encoding sequence may be linked to a control sequence in the sense direction or antisense direction and then may be operated. As one preferable example, the expression vector according to the present invention includes polynucleotide encoding the novel peptide tag, for example any one of polynucleotide having a base sequence as set forth in SEQ ID NO: 7 or polynucleotide having a base sequence as set forth in SEQ ID NO: 8, and target polynucleotide encoding target protein.

Another aspect of the present invention relates to fusion protein including the above mentioned novel peptide tag. In the present invention, the term "fusion protein" means polymer in a type of linking at least two peptides, oligopeptides, polypeptides, or proteins having different function each other. In the present invention, the fusion protein may be interchangeably used with fusion polypeptide, fusion oligopeptide, recombinant polypeptide, recombinant oligopeptide, or recombinant protein. A first part of the fusion protein according to the present invention includes at least one novel peptide tag mentioned above, and a second part of the fusion protein includes at least one target protein. In the present invention, the target protein may be interchangeably used with target peptide, target oligopeptide, or target polypeptide. The fusion protein according to the present invention may be effectively detected or purified using an antibody to the novel peptide tag because the novel peptide tag is linked to a codon region. The peptide tag according to the present invention may be inserted into anywhere inside protein as long as the tag does not substantially influence on C-terminal, N-terminal, or protein functionalities of the target protein. Here, the meaning of not influencing substantially on the functionalities of the protein is that before fusing the peptide tag, activity of the protein is maintained in 80% or more, and preferably 95% or more. The target protein used in the present invention may include any proteins, and for example, single chain FV (ScFv) of humanization antibody AKA/HzK to a cancer-related antigen, TAG-72, thrombopoietin (TPO), B-lymphocyte stimulator, and the like. The fusion protein according to the present invention may include at least two peptides combination, for example, a combination of peptide tag and target protein, and at least two peptides may be bound by a covalent bond or non-covalent bond. At this time, the peptide tag and target protein may be directly bound without any mediators each other, or may be indirectly bound each other by a mediator, such as a peptide linker. As a preferable example, when the fusion protein includes at least one cleavageable peptide linker, target protein can be collected from the fusion protein by chemically and/or enzymatically cleaving the cleavageable linker. Accordingly, the fusion protein according to the present invention may be preferably designed to include at least one tag, cleavageable peptide linker, and target protein. Generally, the linker allows proteins to be combined or to have minimum gap therebetween or to maintain other spartial relationships, but does not have biological activity. However, the peptide linker composition amino acid may be selected to partially influence on molecular properties, such as folding, net charge, or hydrophobicity. The peptide linker may selectively include a region for isolating the fused composition polypeptide, for example, the region capable of being cleaved by protease. The cleavageable peptide linker may have a length of 1 to about 50 amino acids, and preferably 1 to about 20 amino acids. The peptide linker that can be cleaved by enzyme may include, for example, caspase-3 cleavage sequence, and the peptide linker that can be cleaved by acid may include, for example, aspartic acid-proline dipeptide (D-P) moiety. The cleavageable peptide linker may be incorporated into the fusion protein using many techniques that are well known in the art. In addition, a flexible peptide linker may be used, and a peptide linker having a GGSGGT (SEQ ID NO: 55) amino acid sequence, a GGGGS (SEQ ID NO: 56) amino acid sequence, and a GGGGSGGGGS (SEQ ID NO: 57) amino acid sequence may be used. However, the present invention is not limited thereto. The peptide linker allows the polynucleotide including the peptide linker to be operably linked in frame between the polynucleotides encoding the respective peptides of the fusion protein, and then to express through an expression vector.

In the present invention, the means for preparing peptide (peptide tag, cleavageable peptide linker, target peptide, and/or fusion protein) are well known in the art [see Stewart etal., Solid Phase Peptide Synthesis, Pierce Chemical Co., Rockford, Ill., 1984; Bodanszky, Principles of Peptide Synthesis, Springer-Verlag, N.Y., 1984; and Pennington etal., Peptide Synthesis Protocols, Humana Press, Totowa, N.J., 1994]. Various composition elements (tag peptide, target peptide, cleavageable linker, and the like/cleavage sequence) of the fusion protein described in the present specification may be prepared by the known chemical synthesis method [see Hermanson, Greg T., Bio-conjugate Techniques, Academic Press, New York (1996)]. However, the chemical synthesis is often limited to peptide having a length of about less than 50 amino acids because of costs and/or impurities. The peptide described in the present specification may be preferably prepared by using a standard recombinant DNA and molecular cloning technique [see Sambrook, J. et al., Molecular Cloning: A Laboratory Manual, Third Edition, Cold Spring Harbor Laboratory Press, Cold Spring Harbor, N.Y. (2001); Silhavy, T. J., et al., Experiments with Gene Fusions, Cold Spring Harbor Laboratory Cold Press Spring Harbor, N.Y. (1984); and Ausubel, F. M. et. al., Short Protocols in Molecular Biology, 5th Ed. Current Protocols and John Wiley and Sons, Inc., N.Y., 2002]

Another aspect of the present invention relates to a transformant including the above mentioned expression vector. In the present invention, the term "transformant" means the cell transformed by introducing the expression vector including the polynucleotide encoding at least one target protein into a host cell. A method of preparing transformant by introducing the expression vector into a host cell includes a chemical treatment method such as transient transfection, micro injection, transduction, cell fusion, calcium phosphate precipitation, liposemmediated transfection, DEAE Dextran-mediated transfection, polybrene-mediated transfection, electroporation, electroinjection, and PEG, and a method using a gene gun, and the like. However, the present invention is not limited thereto. The fusion protein can be prepared in quantity and also isolated when the transformant introduced with the expression vector is cultured in a nutrient medium. A medium and culture conditions may be used through a proper selection of common use according to host cells. At the time of culturing, conditions such as temperature, pH of medium and culture time should be properly controlled to be suitable for growth and development of cells and a bulk production of protein. As a host cell that can be transformed by the expression vector according to the present invention, the kinds thereof is not largely limited as long as procaryotic cells, plant cells, insect cells, animal cells, and the like are known in the art. Preferably, the host having high DNA transduction efficiency and high transducted DNA expression efficiency is generally used as a host cell. Examples of the host cell may include well-known procaryotic hosts such as *Escherichia, Pseudomonas, Bacillus*, and *Streptomyces*, and preferably *E. coli* may be used. The expression of protein by a host cell may be induced by using isopropyl-1-thio-β-D-galactopyranoside (IPTG) that is an inducer, and the induction time may be controlled to maximize protein amount. The protein recombinantly produced in the present invention may be collected from a medium or cell lysate. When the recombinant protein is a membrane-binding type, the recombinant protein may be isolated from the membrane by using a suitable surfactant solution (for example, Triton-X 100) or enzamatically cleaving. The cell used for a protein expression may be destructed by various physical or chemical means such as frozen-thaw repetition, sonication, mechanical destruction, or a disintegrating agent of cells, and also may be isolated or purified by the general biochemical isolation technique (Sambrook etal., Molecular Cloning: A laborarory Manual, 2nd Ed., Cold Spring Harbor Laboratory Press, 1989; Deuscher, M., Guide to Protein Purification Methods Enzymology, Vol. 182. Academic Press. Inc., San Diego, Calif, 1990). For example, a method for isolating or purifying the protein expressed by a host cell includes electrophoresis, centrifugation, gel filtration, precipitation, dialysis, chromatography (ion-exchange chromatography, affinity chromatography, immunoadsorption affinity chromatography, reverse phase HPLC, gel permeation HPLC), iso-electricity focus, and various modifications and complex methods thereof, but the present invention is not limited thereto. Meanwhile, the fusion protein including the peptide tag according to the present invention may be preferably isolated and purified by using an immunoabsorption affinity chromatography using an antibody to the peptide tag.

Another aspect of the present invention relates to an antibody to the above mentioned peptide tag and a hybridoma cell line capable of producing the antibody. The antibody according to the present invention is an antibody that can specifically recognize the peptide having an amino acid sequence as set forth in SEQ ID NO: 1 or the peptide having an amino acid sequence as set forth in SEQ ID NO: 2, or can be specifically or selectively bound to the peptides. In the present invention, the term "antibody" means a substance produced by stimulation of a specific antigen in an immune system, and includes functional fragments in a natural type produced in an immune system and also an antibody molecule having the same activity as the natural type, in which the fragments can generate an antigen-antibody reaction through specifically binding with the specific antigen. The antibody in the natural type generally has a structure of two light chains and two heavy chains, in which the respective light chains are bound to the heavy chains in a disulfide bond. The functional fragments of the antibody molecule mean the fragment having an antigen binding function, and include Fab, F(ab'), F(ab')2, Fv, and the like. Fab among the antibody fragments has a structure having variable regions of light chain and heavy chain, invariant region of light chain, and first invariant region of heavy chain (CH1), and has one antigen binding region. Fab' is different from Fab because it has a hinge region including at least one cysteine residue at C-terminal of heavy chain CH1 domain. F(ab')2 is produced by a disulfide bond of cysteine residue of the hinge region of Fab'. Fv is the minimum antibody fragment having only the heavy chain variable region and light chain variable region, and a recombinant technique for producing the Fv fragment is disclosed in WO 88/10649, WO 88/106630 A, WO 88/07085 A, WO 88/07086 A and WO 88/09344 A. For a double chain Fv (dsFv), the heavy chain variable region and light chain variable region are linked by a disulfide bond and for a single chain Fv (scFv), the heavy chain variable region and light chain variable region are generally linked by a covalent bond through a peptide linker. The antibody fragments may be obtained by protease [for example, Fab may be obtained by a restriction-cleavage of the whole antibody using a papain and F(ab')2 fragment may be obtained by a restriction-cleavage of the whole antibody using a pepsin], and preferably prepared by a gene recombinant technique. For purposes of the present invention, the antibody may be an antibody capable of being specifically bound to the peptide tag of the present invention, preferably a Fab type or whole antibody type, and more preferably a monoclonal antibody type. In addition, the present invention provides a hybridoma cell line capable of producing a monoclonal antibody to the novel peptide tag as described above. The hybridoma cell line has been registered to Korean Collection for Type Culture (KCTC), Korea Research Institute of Bioscience and Biotechnology, Korea Research Institute of Bioscience and Biotechnology (KRIBB), 125 Gwahak-ro, Yuseong-gu, Daejeon 305-806, Republic of Korea, on Sep. 24, 2012, and has a deposition number of KCTC 12283BP.

The monoclonal antibody having a specific binding to the novel peptide tag of the present invention may be prepared by using the peptide tag or polypeptide including the peptide tag as an immunogen. More specifically, an immune sensitization is performed by injecting the peptide tag as an immunogen into subcutaneous, muscle, vein, or abdominal cavity of nonhuman mammals one time or more. At this time, the peptide tag is used in a type of being mixed with Freund adjuvant if necessary. Preferably, the nonhuman mammals include a mouse, rat, hamster, guinea pig, rabbit, cat, dog, pig, goat, sheep, donkey, horse, cow, and the like, and include transgenic animals genetically modified to produce an antibody derived from other animals, such as a transgenic mouse producing a human antibody. More preferably, the mouse, rat, hamster, guniea pig, or rabbit is used. The immunities are performed one to four times per day for about 1 to 21 days from the primary immunity, and after about 1 to 10 days from the final immunity, the cell producing the antibody can be obtained from an immune-sensitized mammal. The number of immunity and time interval may be properly changed by immunogen properties. The preparation of hybridoma secreting the monoclonal antibody may be performed according to Kira and milstein method (Nature, 1975, Vol. 256, p. 495-497) and the corresponding methods. The hybridoma cell may be prepared by fusing cells producing an antibody, in which the cells producing an antibody are included in any one selected from the group consisting of spleen, lymph node, bone marrow, and tonsil collected from the nonhuman mammal that is immuno-sensitized as mentioned above and preferably spleen, and myelomma cells derived from a mammal without autoantibody-producing ability. The myeloma cells used for the above cell-fusion may include mouse-derived myleoma cells P3/X63-AG8. 653(653), P3/NSI/1-Ag4-1 (NS-1), P3/X63-Ag8. U1(P3U1), SP2/0-Ag14(Sp2/O, Sp2), PAI, F0, or BW5147; rat-derived myeloma cells 210 RCY3-Ag. 2.3; or human-derived myeloma cells U-266 AR1, GM1500-6TG-A1-2, UC729-6, CEM-AGR, D1R11 or CEM-T15. The cell fusion may be performed by using a fusion accelerator, such as polyethylene glycol or Sendai virus, or a method using electric pulse, for example. For example, the antibody-producing cells and mammal-derived cells capable of being unlimited prolifered are floated in a ratio of about 1:1 to 1:10 in a fusion medium including a fusion accelerator, and then cultured at about 30 to 40° C. for about 1 to 5 minutes. As a fusion medium, for example, a general medium such as a MEM medium, RPMI1640 medium, and Iscove's Modified Dulbecco's Medium may be preferably used, and it is preferable to use the medium without serum such as bovine serum. As a method of screening hybridoma cell clones producing a monoclonal antibody, the obtained fusion cells are transferred to a medium for selection such as a HAT medium, cultured at about 30 to 40° C. for about 3 days to 3 weeks, and then the cells except the hybridoma cells are killed. Subsequently, the hybridoma cells are cultured in a microtiter plate and the reactivity between the immunogen used for the immune reaction of nonhuman animal as mentioned above and culture supernatant is confirmed through an immunoassay such as a radioactive substance-marked immuno antibody (RIA) or Enzyme-Linked Immunosorbent Assay (ELISA). Then, the hybridoma cells having increased reactivity are selected. The selected hybridoma cell clones producing the monoclonal antibody exhibits a specific binding to the immunogen. The monoclonal antibody of the present invention may be obtained by culturing the hybridoma cell line invitro and invivo. A general method for culturing cells derived from mammals is used for culturing, and in order to collect monoclonal antibodies from culture, and the like, a general method for purifying a general antibody in the art is used. Examples of a method for purifying an antibody may include salting out, dialysis, filtration, concentration, centrifugation, fractional precipitation, gel filtration chromatography, ion-exchange chromatography, affinity chromatography, high pressure liquid chromatography, gel electrophoresis, isoelectric electrophoresis, and the like, and a combination thereof if necessary. Since then, the purified monoclonal antibody is concentrated, dried, and then stored in a liquid phase or solid phase according to use. In addition, the monoclonal antibody of the present invention may be expressed by synthesizing the genes, in which the DNAs encoding heavy chain and light chain variable regions are respectively linked to base DNAs (For example, JP 2007-252372 A), through a PCR method or chemical synthesis; introducing the synthesized gene into a known expression vector [for example, pcDNA 3.1 (available from Invitrogen)]; preparing transformant using the expression vector; and then culturing the host cell such as the transformed CHO cell or *E. coli*, and may be obtained by purifying the expressed antibody from the culture solution using Protein A column, and the like.

Another aspect of the present invention relates to uses of the above mentioned novel peptide tag, polynucleotide encoding the peptide tag, or an antibody to the peptide tag.

For example, an example of the present invention provides a method of preparing fusion protein as described above. The method of preparing the fusion protein according to an example of the present invention includes expressing the fusion protein by culturing the transformant introduced with polynucleotide encoding the fusion protein. At this time, the polynucleotide encoding the fusion protein in a type of being included in the recombinant vector is preferably introduced into the transformant. In addition, the recombinant vector includes polynucleotide encoding the peptide tag and target polynucleotide encoding the target protein ligated thereto. At this time, the above two polynucleotide may be preferably ligated by a coding sequence of a peptide linker including a region capable of being cleaved by protease, and the like.

In addition, an example of the present invention provides a method of detecting the above mentioned fusion protein. The method of detecting the fusion protein according to an example of the present invention includes contacting and binding the fusion protein ligating the peptide tag and target protein to an antibody to the peptide tag; and confirming whether or not the fusion protein is ligated to the antibody or analyzing the amount of the fusion protein ligated to the antibody. At this time, specific example of the method of detecting the fusion protein according to an example of the present invention may include a western blotting, Enzyme-linked immunosorbent assay (ELISA), immunoprecipitation, immunofluorescence, immunocytochemistry, protein micro array, and the like. At this time, the protein micro array prepared by fixing specific antibodies to the peptide tag of the present invention on a glass substrate or silicon substrate may be used for analyzing large scale samples.

In addition, an example of the present invention provides a method of purifying the above mentioned fusion protein. The method of purifying the fusion protein according to an example of the present invention includes contacting and binding the fusion protein ligating the peptide tag and target protein to an antibody to the peptide tag; and collecting the fusion protein bound to the antibody. At this time, an antibody is fixed to a support, and preferably a solid support. Examples of the support for fixing an antibody include a column, beads, an absorbent, a nitrocellulose paper, and the like, and an antibody may be fixed to a support through various known fixation methods. Specific examples of the method for purifying the fusion protein according to the present invention include contacting the sample including the tagged protein to the support fixed with the antibody. At this time, the tagged protein is protein that the target protein is covalently bound to the peptide tag, in which the peptide tag has specific binding activity to an antibody, and the contact is generated under a condition of binding an antibody to the peptide tag. Since then, a method of purifying the fusion protein according to the present invention may include removing components that are not bound to the antibody and isolating the tagged protein from the support. At this time, the support and antibody fixed thereto are used as a medium for an immuaffinity chromatography. The immunoaffinity column chromatography may be performed by using the column packed with the medium. The high-purity purified fusion protein can be obtained by using the purification method of the present invention, and thus the original functions of the target protein included in the fusion protein can be maintained.

In addition, an example of the present invention provides a kit for expressing, detecting, or purifying fusion protein. The kit for expressing, detecting, or purifying the fusion protein according to the present invention includes any one selected from the group consisting of the above mentioned novel peptide tag, polynucleotide encoding the peptide tag, a pair of primers for synthesizing the polynucleotide, a re-combinant vector including the polynucleotide, and a transformant transformed by the polynucleotide or recombinant vector. In addition, the kit for expressing, detecting, or purifying the fusion protein according to the present invention may include any one selected from the group consisting of antibodies to the above mentioned novel peptide tag or hybridoma cell lines producing the antibodies. In addition, the kit for expressing the fusion protein according to the present invention preferably includes a recombinant vector including the polynucleotide encoding the novel peptide tag of the present invention. In addition, the kit for detecting or purifying the fusion protein according to the present invention preferably includes an antibody to the novel peptide of the present invention. At this time, the recombinant vector constituting the kit may be preferably an expression vector including polynucleotide encoding the fusion protein, or may be preferably provided in a type capable of easily preparing the expression vector by a user. The fusion protein is polypeptide, in which the peptide tag and target protein are ligated. In addition, the antibody constituting the kit is preferably provided in a type of being fixed on a proper support. In addition, preferably, the kit for detecting the fusion protein may further include means capable of detecting an antibody to the peptide tag. At this time, the means of detecting the antibody of the present invention is preferably a secondary antibody. In addition, the antibody or secondary antibody of the present invention, constituting the kit for detecting the fusion protein, may be preferably marked with a marker such as enzyme, radioactive substances, a fluorescent material, and the like, and a method of marking is preferably a conjugation. In addition, the kit for purifying the fusion protein may further include protease for isolating the peptide tag. Furthermore, the kit according to the present invention may further include directions, restriction enzymes, ligase, buffer solutions, and the like.

Hereinafter, the present invention will be described in more detail with reference to Examples. However, the following Examples are only for clearly exemplifying the technique properties of the present invention and the claimed range of the present invention is not limited to these Examples.

EXAMPLE 1

Cloning of BphP Gene and BphN Gene of *Deinococcus radiodurans*

A gene (SEQ ID NO: 4) encoding the whole length of Bacterophytochrome protein (BphP) of *Deinococcusradiodurans* and a gene (SEQ ID NO: 5) encoding polypeptide (BphN) having amino acids located at 1 to 321 locations based on N-terminal of DrBphP were cloned by using a PCR. Specifically, the PCR was performed about 30 cycles by using a gene (SEQ ID NO: 4) encoding the whole length of Bacteriophytochrome protein (BphP) of *Deinococcusradiodurans* as a template, primers for cloning the BphP gene or primers for cloning the BphN gene, and Ex-Taq (TAKARA) polymerase to obtain the amplified BphP DNA product and BphN DNA product. The primers used for obtaining the amplified BphP DNA product and BphN DNA product are listed in the following Table 1. The primers listed in the following Table 1 and all the primers to be described below were prepared by asking to Bioneer co. (KR).

TABLE 1

| SEQ ID NO: | Types of Primer | Base Sequence (5'→3') | Restriction enzyme recognition site included in primer |
|---|---|---|---|
| 9 | Forward primer for cloning BphP | GCCATATGATGAGCCGGGACCC GTTGCCC | Nde I |
| 10 | Reverse primer for cloning BphP | GCCTCGAGTCAGGCATCGGCGG CTCCCGG | Xho I |
| 11 | Forward primer for cloning BphN | GCCATATGATGAGCCGGGACCC GTTGCCC | Nde I |
| 12 | Reverse primer for cloning BphN | GCCTCGAGCGCTTCCTTGACCT GAACTTG | Xho I |

The amplified PCR products were subjected to a running on 1% agarose gel (QA-Agarose gel™, Q-BIO, CAT #AGAH0250), and then a size of amplified DNA was confirmed through an ultraviolet irradiator. Since then, only the bands corresponding to the DNA amplification products on the gel were cut out, the desired DNAs were only isolated by using a gel elution kit (FavorPrep GEL/PCR purification mini kit, FAVORGEN, CAT #FAGCK001-1), the desired DNAs were bound to Easy T-vector (promega), and then the base sequences were determined by asking to Bioneer co. (KR). As a result, it was confirmed that the DNA product produced from the PCR had the BphP DNA and BphN DNA that were desired base sequences.

Since then, each of the amplified BphP DNA product and BphN DNA product was inserted into a pET28a(+) vector (Manufacturer: Novagen) by using a restriction enzyme, Nde I and Xho I, transformed by applying heat shock at 42° C. for 1 minute to a BL21 competent cell (Manufacturer: RBC, Taipei, Taiwan) that was *E. coli*, and cultured on a LB medium including kanamycin to express BphP protein and BphN protein.

EXAMPLE 2

Expression of BphP Protein and BphN protein of *Deinococcus radiodurans*

Colonies transformed to the BL21 competent cell and grown on the LB medium were inoculated to a LB medium including kanamycin, and then seed-cultured at 37° C. for about 8 hours. The seed-cultured cells were inoculated in the LB medium including kanamycin; the cells were cultured until a value measured at $OD_{600}$ became 0.6; then IPTG (isopropyl-1-thio-β-D-galactopyranoside) was added to be 0.5 mM of the total concentration; and the protein expression was induced at 25° C. for 6 hours. Since then, the cells were centrifuged to remove supernatant and then pellet was re-suspended in a binding buffer (100 mM of Tris-Cl, 150 mM of NaCl, and 10 mM of imidazole, pH 8.0). Then, the re-suspended pellet was sonicated to break the cells, again centrifuged to remove only supernatant, and then the protein was purified by using a $Ni^+$-NTA column (QIAGEN). Since then, the purified protein was stored at −70° C.

Since the BphP protein and BphN protein include all the PAS, GAF domain, and Cys-24 residue that play an important role in a BV binding, the proteins themselves are possible to be bound to the BV. The biliverdin (BV, 2 μm/ml, Frontier, Scientific, Carnforth, UK) was added to Apo-BphP protein and Apo-BphN protein that were purified in order to obtain holo-BphP protein, and then reacted at room temperature for 10 minutes. Since then, the reaction samples were subjected to a SDS-PAGE, reacted in a zinc acetate solution (20 mM of zinc acetate, 150 mM of Tris-Cl, pH 7.0) for 20 minutes, and then the fluorescence signals of the proteins were observed under UV. In addition, the reaction samples were subjected to a SDS-PAGE, and then subjected to a coomassie staining. The left of (B) in FIG. 1 shows a result of the coomassie staining, and the right of (B) in FIG. 1 shows a result of a zinc blotting. As shown in (B) of FIG. 1, it could be confirmed that the BphP protein and BphN protein were smoothly expressed and purified.

EXAMPLE 3

Preparation of Monoclonal Antibody Specifically Binding to BphP Protein and BnhN Protein of *Deinococcus radiodurans*

3-1: Immune Treatment

The purified BphP protein or BphN protein as an antigen was mixed with a complete Freund's adjuvant, and then injected into the abdominal cavity of a 6-week female BALB/c mouse. An immersion was mixed by using a vortexer for 1 hour, then mixed with an incomplete Freund's adjuvant and an antigen by using the same method as described above, and then injected into the abdominal cavity. After 2 weeks, blood was collected from the tail of mouse and tested by using a ELISA. When an antibody titer is 1.0 or more at 1/1000, the blood was used for a cell fusion. At 4 weeks from a secondary immune treatment for the cell fusion, the equivalent antigen was diluted with a PBS, and then injected into the abdominal cavity. After 3 days, the mouse was sacrificed and then subjected to the cell fusion.

3-2: Cell Fusion for Production of Monoclonal Antibody

As a B lymphocyte cell origin, a spleen was isolated from fats or other organs after an abdominal incision and was aseptically removed without excessive bleeding. Then the spleen was homogenized by using a cell strainer, diluted with a basic medium, and then centrifuged twice to wash. The B lymphocyte and myeloma cell were mixed in a proper ratio and centrifuged for 5 minutes to remove out the supernatant. Then, the remained cell mixture was lightly shaken, 10 ml of a RBC lysis buffer solution that was warmed up in advance was added, suspended and cultured at 37° C. for 20 minutes. Then, FBS was added to the cultured mixture and then centrifuged. The cell fusion was performed as follows. First, PEG (polyethlyene glycerol) 1500 solution was slowly added to the centrifuged cell mixture in a state of maintaining at 37° C., and then the basic medium was again added to stop the reaction. Since then, the centrifugation was promptly performed to remove out the supernatant; the rest cell mixture was carefully suspended in a microphage medium and divided into a 96 well tissue culture plate; and then cultured in a carbon dioxide constant temperature incubator under a condition of 37° C.

3-3: Selection of Fusion Cell

At 5 days after performing the cell fusion, a HAT medium that was a selection medium for a fusion cell was added to each of the wells. Since then, the HAT medium was added three-day interval using the same method. After 11 days of cell fusion, the HT medium prepared by adding a HT supplement to the complete medium was exchanged and observed daily by using a microscope to confirm a growth degree of the fusion cell. The supernatant in the well that was confirmed to be grown was collected and the antibody production in the supernatant was confirmed by using an ELISA. First, the fusion cell lines that were determined to secrete a desired antibody were subjected to 1st, 2nd and 3rd cloning with a restriction dilution method and thus allowed the fusion cell group to be clone derived from one cell line.

3-4: Selection of Fusion Cell by ELISA

After the cell fusion for determining whether or not the immunity to the antigen immunized was present and preparing a monoclonal antibody, the antigen protein solution diluted with an ELISA coating buffer solution was added to a 96 well tissue culture plate in order to select fusion cells, and then reacted at 4° C. Since then, the antigen protein solution was removed out by suction; then a blocking solution was added to the surfaces of the respective wells; and reacted at 37° C. for 1 hour. Since then, the blocking solution was removed and then washed with a PBST solution three times. The fusion cell culture supernatant was added to the respective wells and reacted at 37° C., and then the solution was removed and washed with a PBST solution three times. The solution prepared by diluting Horseradish peroxidase (HRP) conjugated anti-mouse immunoglobulin (anti-mouse IgG) with a PBS was added to the respective wells. A OPD (orthophenylenediammine dihydrochloride) substrate solution was added to the wells and reacted at room temperature for 10 minutes, and then a stop solution was added to stop the reaction. At this time, in order to confirm a coloring degree after reacting, absorbance was measured at 492 nm with an ELISA reader, and total 24 candidates hybridoma cell line clones were selected based on the measured results.

3-5: Re-Confirmation of Degree of Binding With Antigen Through Fusion Plate ELISA Test and Purification of Antibody With the total 24 candidates hybridoma cell line clones, the BphP protein and BphN protein that were injected as an antigen were used to perform the Fusion plate ELISA test. As a result, the binding degree was confirmed. The results are shown in the following Table 2. As can be seen in the following Table 2, it was estimated that since a 2B8 clone and 2C11 clone were colored in a high level in all the BphP protein and BphN protein of *Deinococcus radiodurans*, the 2B8 clone and 2C11 clone recognized N-terminal region of the BphP protein. However, a 3B2 clone and 3D2 clone were colored in a high level in the BphP protein, but exhibited a value of almost 0 in the BphN protein. Thus, it was estimated that the 3B2 clone and 3D2 clone recognized C-terminal region of the BphP protein. Unlike them, a 3H7 clone was colored in a high level in the BphP protein, but in some low level in the BphN protein. Thus, it was estimated that the 3H7 clone recognized N-terminal region in some degree in addition to C-terminal region of the BphP protein.

Table 2

TABLE 2

| Hybridoma cell line clones | Degree of binding to antigen protein (Absorbance at 492 nm) | |
|---|---|---|
| | BphN | BphP(full) |
| 1B6 | 0.0660 | 1.3190 |
| 1B11 | 0.1560 | 2.3700 |
| 1D6 | 0.0550 | 2.3180 |
| 2B8 | 2.3400 | 2.4200 |
| 2C11 | 2.3480 | 2.4040 |
| 2D9 | 0.1430 | 2.2730 |
| 2E3 | 2.1720 | 1.8020 |
| 2F7 | 0.1220 | 2.4430 |
| 2H8 | 0.0650 | 1.3440 |
| 3A4 | 1.9180 | 2.3770 |
| 3B2 | 0.0980 | 2.2900 |
| 3B3 | 0.0700 | 2.1650 |
| 3C11 | 1.9730 | 2.2590 |
| 3D2 | 0.0640 | 2.2830 |
| 3D10 | 0.1180 | 2.4280 |
| 3D11 | 1.6850 | 2.3130 |
| 3F10 | 0.0730 | 2.3570 |
| 3G2 | 0.0880 | 2.0510 |
| 3G9 | 0.0800 | 1.5580 |
| 3H1 | 1.7840 | 2.0950 |
| 3H7 | 0.4640 | 2.3490 |
| 4B7 | 1.9730 | 2.2620 |
| 4E2 | 0.2050 | 2.3770 |
| 4E3 | 0.0550 | 2.2650 |

Since then, the five hybridoma cell line clones described above were subjected to a first cloning plate ELISA test and then a secondary cloning plate ELISA test, and finally ascites were produced and then antibodies were purified. As a result, five monoclonal antibodies, that is, a 2B8 antibody, 2C11 antibody, 3B2 antibody, 3D2 antibody, and 3H7 antibody were obtained. The antibodies were purified as follows. 0.5 ml of pristane was intraperitoneally injected to a 8-week or more BALB/c mouse. After 1 week or 10 days, hybridoma cells were cultured, washed with a PBS three times, diluted with the PBS to be a concentration of 5 ×10$^6$ cell/0.5 ml, and then injected to the abdominal cavity with a syringe. After observing hydrops abdominis production after 1 week to 10 days, the mouse was sacrificed through dislocation of the cervical vertebra to make a small hole in the abdomen, and then the hydrops abdominis was collected by using a serum separator without flow of the hydrops abdomins. The hydrops abdomins was left at room temperature for about 1 hour, and then centrifuged to remove RBC. A suitable amount of PBS was added to the collected hydrops abdominis and then slowly mixed with ammonium sulfate at 4° C. After centrifuging at 4° C., it was passed through a filter. A suitable amount of beads mixed with Protein A and DFMF was added, and then washed with a tris buffer solution in a 10 times of bed vol. When the antibody was added and well mixed with protein A/G, a fraction was taken and washed with a tris buffer solution; and then glycine was added thereto and eluted many times. The purified antibody was dialyzed through a dialysis bag in the PBS buffer solution for 3 hours; the PBS buffer solution was again exchanged and dialyzed overnight; and then the antibody dialyzed was quantified and then stored.

EXAMPLE 4

Analysis of Monoclonal Antibody Specificity

In order to confirm whether or not the obtained antibodies exhibited the same result to the pre-expressed and purified BphP protein and BphN protein, a western blotting was performed. The respective monoclonal antibodies in a concentration of 1 mg/me as a primary antibody were used with respect to 5 μg of the purified BphP protein and BphN protein in a ratio of 1:1000 based on 2% skim milk; as a secondary antibody, a HRP-mouse antibody (SIGMA) was treated in a ratio of 1:10000; and then a western blotting was performed. As a result, all the 2B8 antibody and 2C11 antibody were bound to the BphP protein and BphN protein, which was the same result in the ELISA test to the hybridoam cell line clones (FIG. 2). Accordingly, it could be considered that all the above two antibodies were bound to the N-terminal region of BphP. Also, bands of the 3B2 antibody and 3D2 antibody were appeared to the BphP protein, but not appeared to the BphN protein. Thus, it could be confirmed that the 3B2 antibody and 3D2 antibody were bound to the C-terminal region of the BphP protein. However, as a result, it could be found that the 3H7 antibody recognized only the BphP protein unlike the result of ELISA test. In addition, for binding degrees of the respective antibodies, the 2B8 antibody and 2C11 antibody binding to the N-terminal region were most strongly bound to the N-terminal region, and the 3D2 antibody recognizing the C-terminal region exhibited weak band as compared with the bands of the 2B8 antibody and 2C11 antibody. Subsequently, the band was strongly exhibited in the order of the 3H7 antibody and 3B2 antibody.

Meanwhile, DrBphP has the structure similar to plant phytochrome, and especially, both the PCDs constituting the N-terminal region have the very similar structures including PAS, GAF, and PHY domains. Thus, whether or not the antibodies were reacted with an oat phytochrome protein was confirmed. However, as a result, it could be confirmed that all the five monoclonal antibodies to the BphP protein of *Deinococcusradiodurans* were not bound to the oat phytochrome protein (Oat PhyA) (FIG. 3). Therefore, it could be confirmed that the monoclonal antibodies to the BphP protein of *Deinococcus radiodurans* were new antibodies specific to BphP, in which the antibodies recognized epitope different from the antibodies to the conventional Oat phytochrome protein.

The present inventors registered the hybridoma cell line 2B8 of 2B8 antibody that was most strongly bound to the monoclonal antibodies to the BphP protein of *Deinococcusradiodurans* to Korean Collection for Type Culture (KCTC), Korea Research Institute of Bioscience and Biotechnology on Sep. 24, 2012, and the hybridoma cell line 2B8 has a deposition number of KCTC 12283BP. Also, the isotype of 2B8 antibody was determined by an ELISA method using a mouse antibody. The heavy chain isotype of 2B8 antibody was IgG 2a and light type isotype of 2B8 antibody was K (kappa).

EXAMPLE 5

Epitope Mapping for Determining Epitope of 2B8 Monoclonal Antibody 5-1: First Epitope Mapping In order to confirm the epitope of 2B8 antibody that was most strongly bound among the monoclonal antibodies to the BphP protein of *Deinococcus radiodurans*, DrBphP recombinant partial peptide was prepared and epitope mapping was performed.

First, in order to clone DNA encoding an amino acid sequence (SEQ ID NO: 13) at 3 to 12 locations, DNA encoding an amino acid sequence (SEQ ID NO: 1) at 3 to 11 locations, DNA encoding an amino acid sequence at 3 to 10 locations, and DNA encoding an amino acid sequence at 4 to 12 locations based on the N-terminal among the full amino acid sequence (SEQ ID NO: 3) of DrBphP, the respective primers were prepared. A PCR was performed about 30 cycles by using the prepared primers and PrimeSTAR HS (TAKARA, R040) polymerase, and amplified DNA products were obtained. The PCR reaction for the DNA cloning did not need a specific template, and the template for amplification could be obtained by binding of a forward primer and a reverse primer when performing one cycle of PCR. The primers used for performing PCR for obtaining an amplification product of DNA encoding the four DrBphP recombinant partial peptides are shown in the following Table 3.

Table 3

TABLE 3

| SEQ ID NO: | Type of primer | Base sequence (5'→3') | Restriction enzyme recognition site included in primers |
|---|---|---|---|
| 14 | Forward primer for cloning BphP 3-12 a.a. | GC CTCGAG GGATCC ATG CGGGACCCGTTGCCCTTTTTT | BamH I |

TABLE 3-continued

| SEQ ID NO: | Type of primer | Base sequence (5'→3') | Restriction enzyme recognition site included in primers |
|---|---|---|---|
| 15 | Reverse primer for cloning BphP 3-12 a.a. | GC GAGCTC GAATTC TCA AAGCG-GTGGAAAAAAGGGCAA | EcoR I |
| 16 | Forward primer for cloning BphP 3-11 a.a. | GC CTCGAG GGATCC ATG CGGGACCCGTTGCCCTTTTTT | BamH I |
| 17 | Reverse primer for cloning BphP 3-11 a.a. | GC GAGCTC GAATTC TCA CGGTG-GAAAAAAGGGCAACGG | EcoR I |
| 18 | Forward primer for cloning BphP 3-10 a.a. | GC CTCGAG GGATCC ATG CGGGACCCGTTGCCCTTTTTT | BamH I |
| 19 | Reverse primer for cloning BphP 3-10 a.a. | GC GAGCTC GAATTC TCA TG-GAAAAAGGGCAACGGGTC | EcoR I |
| 20 | Forward primer for cloning BphP 4-12 a.a. | GC CTCGAG GGATCC ATG GACC-CGTTGCCCTTTTTTCCA | BamH I |
| 21 | Reverse primer for cloning BphP 4-12 a.a. | GC GAGCTC GAATTC TCA AAGCG-GTGGAAAAAAGGGCAA | EcoR I |

The amplified PCR products were subjected to a running on 1% agarose gel (QA-Agarose gel TM, Q-BIO, CAT#AGAH0250), and then a size of amplified DNA was confirmed through an ultraviolet irradiator. Since then, only the bands corresponding to the DNA amplification products on the gel were cut out, the desired DNAs were only isolated by using a gel elution kit (FavorPrep GEL/PCR purification mini kit, FAVORGEN, CAT #FAGCK001-1), and ligated to a pJET (CloneJET PCR cloning kit, Fermentas, #K1232) vector. Then, about 30 to 50 ul of a DH5 α competent cell (Manufacturer: Invitrogen) that was E. coli was added to about 10 to 20 μl of the binding vector, cultured on an ice for 20 minutes, subjected to a heat shock at 42° C. for 1 minute, recovered again on an ice for 20 minutes, spread on a LB medium plate including ampicilin, and incubated at 37° C. overnight to perform transformation. Since then, when the colonies were grown, the colonies were inoculated in a LB medium including ampicilin and the cells were grown by culturing at 37° C. overnight. Then, the plasmid was extracted from the cells using a plasmid extraction kit (FavorPrep Plasmid Extraction kit, FAVORGEN, cat #FAPDE300). Since then, base sequence of the extracted plasmid was determined by asking to Bioneer co. (KR). As a result, it was confirmed that the DNA product produced by the PCR had the desired based sequence.

Figure 4:
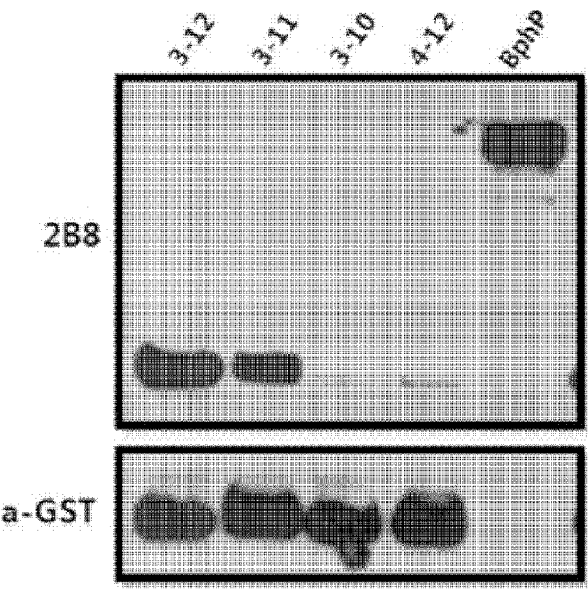
FIG. 4 shows a result of first epitope mapping to the 2B8 antibody through a western blotting.

In addition, after cleaving the extracted plasmid and a pGEX4T 1 vector (GE Healthcare, Piscataway, N.J., USA) having a GST tag autonomously using a restriction enzyme, BamH I and EcoR I, as a target DNA, DNA encoding an amino acid sequence (SEQ ID NO: 13) at 3 to 12 locations, DNA encoding an amino acid sequence (SEQ ID NO: 1) at 3 to 11 locations, DNA encoding an amino acid sequence at 3 to 10 locations, and DNA encoding an amino acid sequence at 4 to 12 locations based on the N-terminal among the full amino acid sequence (SEQ ID NO: 3) of DrBphP were respectively ligated to the pGEX4T1 vector that was a protein expression vector. Since then, a BL21 competent cell (Manufacturer: RBC, Taipei, Taiwan) that was E. coli was transformed to the pGEX4T1 vector including the target DNA, and cultured on a LB medium including ampicilin to induce protein expression. Since then, the cultured cells were sonicated and thus destroyed. After centrifuging the destroyed cells, the resulting supernatant was only isolated, and then the proteins were purified by using a GST resin (Glutathion Sepharose™ High Performance, GE Healthcare). The purified proteins and BphP protein of Deinococcus radiodurans were subjected to a western blotting. At this time, as a primary antibody, a 2B8 monoclonal antibody and anti-GST antibody were used and as a secondary antibody, Horseradish peroxidase (HRP) conjugated anti-mouse immunoglobulin (anti-mouse IgG; Sigma) was used. In addition, in order to develop the samples transferred into the cellulose membrane after the SDS-PAGE, Amersham™ ECL™ Western Blotting Detection Reagents (GE Healthcare, RPN2106OL/AF) were used. FIG. 4 shows a result of performing first epitope mapping to a 2B8 antibody through a western blotting. As can be seen in FIG. 4, it was confirmed that the epitope of the 2B8 antibody was 9 amino acids (SEQ ID NO: 1) corresponding to 3 to 11 locations based on the N-terminal among the full amino acid sequences (SEQ ID NO: 3) of DrBphP, and could be used as a peptide tag. In addition, the peptide tag having an amino acid sequence as set forth in SEQ ID NO: 1 was called "BRT tag".

5-2: Secondary Epitope Mapping

From the first epitope mapping, it was confirmed that the BRT tag having an amino acid sequence as set forth in SEQ ID NO: 1 was the epitope of 2B8 antibody. The present inventors prepared DrBphP modified partial peptide, in which one amino acid residue among the amino acid residues as set forth in SEQ ID NO: 1 was substituted with alanine, in order to confirm an amino acid residue having an important role on binding with the 2B8 antibody among the amino acid residues constituting the BRT tag. Since then, in order to confirm whether or not the 2B8 antibody recognized the DrBphP modified partial peptide, a secondary epitope mapping was performed.

First, in order to clone DNA including an amino acid sequence at 3 to 11 locations based on the N-terminal among the full amino acid sequence (SEQ ID NO: 3) of DrBphP and at the same time, encoding peptide (referred to as R3A), in which arginine, third amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as D4A), in which aspartic acid, fourth amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as P5A), in which proline, 5th amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as L6A), in which leucine, 6th amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as P7A), in which proline, 7th amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as F8A, SEQ ID NO: 2), in which phenylalanine, 8th amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as F9A), in which phenylalanine, 9th amino acid residue was substituted with alanine; DNA including an amino acid sequence at 3 to 11 locations based on the N-terminal among the full amino acid sequence (SEQ ID NO: 3) of DrBphP and at the same time, encoding peptide (referred to as P10A, SEQ ID NO: 36), in which proline, 10th amino acid residue was substituted with alanine; and DNA including an amino acid sequence at 3 to 11 locations based on the N-terminal among the full amino acid sequence (SEQ ID NO: 3) of DrBphP and at the same time, encoding peptide (referred to as P11A), in which proline, 11th amino acid residue was substituted with alanine, the respective primers were prepared. A PCR was performed about 30 cycles by using the prepared primers and PrimeSTAR HS (TAKARA, R040) polymerase, and amplified DNA products were obtained. The PCR reaction for the DNA cloning did not need a specific template, and the template for amplification could be obtained by binding of a forward primer and a reverse primer when performing one cycle of PCR. The primers used for performing PCR for obtaining an amplification product of DNA encoding the nine DrBphP recombinant partial peptides are shown in the following Table 4. After obtaining the DNA amplification products by the PCR, the process will not be provided because it is same as the first epitope mapping.

Table 4

TABLE 4

| SEQ ID NO: | Type of primer | Base sequence (5'→3') | Restriction enzyme recognition site included in primer |
|---|---|---|---|
| 22 | Forward primer for cloning R3A | GC GGATCC ATG GCCGACCCGTTGCC-CTTTTTTCCACCG | BamH I |
| 23 | Reverse primer for cloning R3A | GC GAATTC TCA CGGTG-GAAAAAAGGGCAACGGGTCGGC | EcoR I |
| 24 | Forward primer for cloning D4A | GC GGATCC ATG CGGGCCCCGTTGCC-CTTTTTTCCACCG | BamH I |
| 25 | Reverse primer for cloning D4A | GC GAATTC TCA CGGTG-GAAAAAAGGGCAACGGGGCCCG | EcoR I |
| 26 | Forward primer for cloning P5A | GC GGATCC ATG CGGGACGCCTTGCC-CTTTTTTCCACCG | BamH I |
| 27 | Reverse primer for cloning P5A | GC GAATTC TCA CGGTG-GAAAAAAGGGCAAGGCGTCCCG | EcoR I |
| 28 | Forward primer for cloning L6A | GC GGATCC ATG CGGGACCCGGCCCC-CTTTTTTCCACCG | BamH I |
| 29 | Reverse primer for cloning L6A | GC GAATTC TCA CGGTG-GAAAAAAGGGGCCGGGTCCC | EcoR I |
| 30 | Forward primer for cloning P7A | GC GGATCC ATG CGGGACCCGTTGGC-CTTTTTTCCACCG | BamH I |

TABLE 4-continued

| SEQ ID NO: | Type of primer | Base sequence (5'→3') | Restriction enzyme recognition site included in primer |
|---|---|---|---|
| 31 | Reverse primer for cloning P7A | GC GAATTC TCA CGGTGGAAAAAAGGC-CAACGGGTCCCG | EcoR I |
| 32 | Forward primer for cloning F8A | GC GGATCC ATG CGGGACCCGTTGCC-CGCCTTTCCACCG | BamH I |
| 33 | Reverse primer for cloning F8A | GC GAATTC TCA CGGTGGAAAG-GCGGGCAACGGGTCCCG | EcoR I |
| 34 | Forward primer for cloning F9A | GC GGATCC ATG CGGGACCCGTTGCC-CTTTGCCCCACCG | BamH I |
| 35 | Reverse primer for cloning F9A | GC GAATTC TCA CG-GTGGGGCAAAGGGCAACGGGTCCCG | EcoR I |
| 37 | Forward primer for cloning P10A | GC GGATCC ATG CGGGACCCGTTGCC-CTTTTTTGCCCCG | BamH I |
| 38 | Reverse primer for cloning P10A | GC GAATTC TCA CGGGGCAAAAAAGGGCAACGGGTCCCG | EcoR I |
| 39 | Forward primer for cloning P11A | GC GGATCC ATG CGGGACCCGTTGCC-CTTTTTTCCAGCC | BamH I |
| 40 | Reverse primer for cloning P11A | GC GAATTC TCA GGCTG-GAAAAAAGGGCAACGGGTCCCG | EcoR I |

Figure 5:
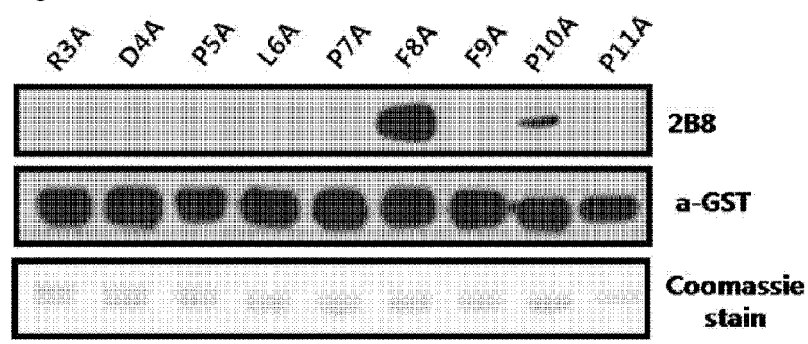
FIG. 5 shows a result of second epitope mapping to the 2B8 antibody through a western blotting and coomassie staining.

FIG. 5 shows a result of performing a secondary epitope mapping to the 2B8 antibody through a western blotting and coomassie staining. As can be seen in FIG. 5, it could be confirmed that other epitopes of 2B8 antibody was the peptide (referred to as "F8A", SEQ ID NO: 2) including an amino acid sequence at 3 to 11 locations based on the N-terminal among the full amino acid sequence (SEQ ID NO: 3) of DrBphP, in which at the same time, phenylalanine, 8th amino acid residue was substituted with alanine, or the peptide (referred to as "P10A", SEQ ID NO: 36) including an amino acid sequence at 3 to 11 locations based on the N-terminal among the full amino acid sequence (SEQ ID NO: 3) of DrBphP, in which at the same time, proline, 10th amino acid residue was substituted with alanine. Other epitopes of 2B8 antibody can be used as a peptide tag, and especially, the peptide having an amino acid sequence as set forth in SEQ ID NO: 2 was specifically and strongly bound to the 2B8 antibody, and thus was considered as excellent peptide tag.

EXAMPLE 6

Preparation of Fusion Protein Using BRT Tag and Detection of Fusion Protein Using Antibody to BRT Tag The fusion protein was prepared by using the BRT tag of the present invention, and the fusion protein was detected by using a B28 antibody that was a monoclonal antibody to the BRT tag.

6-1: Expression and Detection of Fusion Protein in *E. coli*

In order to confirm whether or not the fusion protein including the BRT tag was normally expressed in *E. coli* and detect whether or not the expressed fusion protein was detected by using the 2B8 monoclonal antibody, a DNA construct encoding the fusion protein prepared by linking the BRT tag in front of the GST (Glutathion-S-Transferase) protein was prepared. In order to clone DNA encoding the BRT tag of the present invention and DNA encoding c-myc tag, the respective primers were prepared. A PCR was performed about 30 cycles by using the prepared primers and PrimeSTAR HS (TAKARA, R040) polymerase, and amplified DNA products were obtained. The PCR reaction for the DNA cloning did not need a specific template, and the template for amplification could be obtained by binding of a forward primer and a reverse primer when performing one cycle of PCR. The primers used in PCR for obtaining the two amplification product of DNAs encoding the two DrBphP recombinant partial peptides are shown in the following Table 5. Only the desired DNA was isolated from the amplified PCR products, and then ligated to a pJET (Clone-JET PCR cloning kit, Fermentas, #K1232) vector. Since then, the base sequences were determined by asking the binding vector to Bioneer co. (KR). As a result, it was confirmed from the PCR that the DNA product had desired base sequences.

Table 5

TABLE 5

| SEQ ID NO: | Type of primer | Base sequence (5'→3') | Restriction enzyme recognition site included in primer |
|---|---|---|---|
| 41 | Forward primer for cloning BRT tag | GCCTCGAGGGATCCATGCGGGACCC GTTGCCCTTTTTT | BamH I |
| 42 | Reverse primer for cloning BRT tag | GCGAGCTCGAATTCTCACGGTGGAA AAAAGGGCAACGG | EcoR I |
| 43 | Forward primer for cloning c-myc tag | GCGGATCCATGGAACAAAAATTAAT TTCTGAAGAAGATTTA | BamH I |
| 44 | Reverse primer for cloning c-myc tag | GCGAATTCTCATAAATCTTCTTCAG AAATTAATTTTTGTTC | EcoR I |

Figure 6:
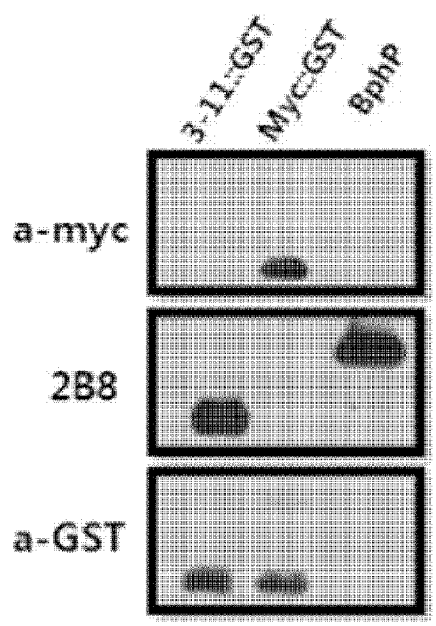
FIG. 6 shows a result of western blotting illustrating whether or not it was possible to normally express the fusion protein, in which a BRT tag was bound to N-terminal of GST protein, on *E. coli* and also it was possible to detect the fusion protein by the 2B8 antibody.

Since then, the isolated DNA product was ligated to pGEX4T1 vector (GE Healthcare, Piscataway, N.J., USA) including DNA encoding a GST (Glutathion-S-Transferase) protein autonomously, in which the vector was an expression vector. Specifically, the isolated DNA product and pGEX4T1 vector ((GE Healthcare, Piscataway, N.J., USA) were cleaved with a restriction enzyme, BamH I and EcoR I and then ligated by using ligase. Since then, the target DNA was transformed to a BL21 competent cell (Manufacturer: RBC, Taipei, Taiwan) using the pGEX4T1 vector by applying heat shock at 42° C. for 1 minute and cultured on a LB medium including ampicilin to express the fusion protein (referred to as 3-11::GST), in which a GST protein was ligated with a BRT tag, and the fusion protein (referred to as Myc::GST), in which a GST protein was ligated with a BRT tag, respectively. Specifically, the colonies transformed to the BL21 competent cells, which were grown on the LB medium, were inoculated to a LB medium including ampicilin, and seed-cultured at 37° C. for about 8 hours. The seed-cultured cells were inoculated to the LB medium; the cells were grown until a value at $OD_{600}$ reached to 0.6; IPTG was added to be a total concentration of 0.5 mM; and then the protein expression was induced at 25° C. for 6 hours. Since then, the protein was purified by using a GST resin (Glutathion Sepharose™ High Performance, GE Healthcare) that was available commercially. A western blotting was performed with the purified proteins and BphP protein of *Deinococcusradiodurans*. At this time, a 2B8 monoclonal antibody and anti-myc antibody were used as a primary antibody and Horseradish peroxidase (HRP) conjugated anti-mouse immunoglobulin (anti-mouse IgG; Sigma) was used as a secondary antibody. In addition, in order to develop the samples transferred to the cellulose membrane after performing a SDS-PAGE, Amersham™ ECL™ Western Blotting Detection Reagents (GE Healthcare, RPN2106OL/AF) was used. FIG. 6 shows a result of western blotting illustrating whether or not it was possible to normally express the fusion protein, in which a BRT tag was bound to N-terminal of GST protein, on *E. coli* and also it was possible to detect the fusion protein by the 2B8 antibody. As can be seen in FIG. 6, the fusion protein having the BRT tag bound to the N-terminal was smoothly expressed in *E. coli* and the expressed fusion protein was detected in a satisfactory level by the 2B8 antibody. In addition, the epitope tagging system using the BRT tag and 2B8 antibody exhibited the effect at an almost equal level as compared with the epitope tagging system using a c-myc tag that was generally used and an antibody thereto.

6-2: Expression and Detection of Fusion Protein in Plant Cells

In order to confirm whether or not the fusion protein including the BRT tag was normally expressed on the plant cells and also whether or not the expressed fusion protein was detected with the 2B8 monoclonal antibody, a DNA construct encoding the fusion protein having the BRT tag bound in front of the GFP (Green Fluorescent Protein) was prepare. In order to clone DNA encoding the fusion protein having the BRT tag of the present invention bound to the GFP (referred to as BRT::GFP) and DNA encoding the fusion protein having a c-myc tag bound to the GFP (referred to as Myc::GFP), the respective primers were prepared. A PCR was performed about 30 cycles using the prepared primers and PrimeSTAR HS (TAKARA, R040) polymerase and the DNA (SEQ ID NO: 45) encoding the GFP was used as a template for the PCR. The primers used for performing the PCR to obtain two DNA amplification products are listed in the following Table 6. The desired DNA was only isolated from the amplified PCR products, and then ligated to a pJET (CloneJET PCR cloning kit, Fermentas, #K1232) vector. Since then, the base sequence was measured by asking the binding vector to Bioneer co.(KR). As a result, it was confirmed that the DNA products obtained from the PCR had the desired base sequences.

Table 6

TABLE 6

| SEQ ID NO: | Type of Primer | Base sequence (5'→3') | Restriction enzyme recognition site included in primer |
|---|---|---|---|
| 46 | Forward primer for cloning BRT::GFP | GCCTCGAGATGAGGGATCCACTTCCA TTCTTCCCTCCAATGGTGAGCAAGGG CGAG | Xho I |
| 47 | Reverse primer for cloning BRT::GFP | GCGAGCTCTTACTTGTACAGCTCGTC CAT | Sac I |

TABLE 6-continued

| SEQ ID NO: | Type of Primer | Base sequence (5'→3') | Restriction enzyme recognition site included in primer |
|---|---|---|---|
| 48 | Forward primer for cloning Myc::GFP | GGAGAGGACCTCGAGATGGAACAAAA GCTTATTTCTGAAGAAGATCTTATG GTGAGCAAGGGCGAG | Xho I |
| 49 | Reverse primer for cloning Myc::GFP | GCGAGCTCTTACTTGTACAGCTCGTC CAT | Sac I |

Figure 7:
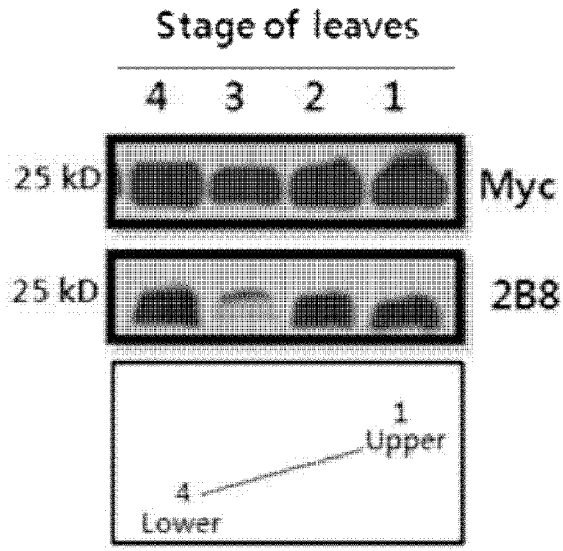
FIG. 7 shows a result of western blotting illustrating whether or not it was possible to normally express the fusion protein, in which a BRT tag was bound to N-terminal of GST protein, on a plant cell and it was possible to detect the fusion protein by the 2B8 antibody.

Since then, the isolated DNA products were ligated to a pBY030.2R vector that was an expression vector, and then an Agrobacterium LBA4404 cell was transformed by using the vector. Since then, the Agrobacterium LBA4404 was injected to the bottom side of leaves of Nicotianabenthamiana(tobacco) plant body using a syringe, and then the fusion protein ligating the BRT tag (referred to as BRT::GFP) and the fusion protein having the c-myc tag ligated to the GFP (referred to as Myc::GFP) were respectively transient-expressed on the tobacco plant body. The detailed experiment method can be seen in Imogen et al (NATURE PROTOCOL, 2006, Vol.1, NO.4, 2019-2025). After culturing Agrobacterium until reaching to 0.7 values at $OD_{600}$, the Agrobacterium was injected to the plant body; then the body plant was maintained in a culture room for 5 days; and then the samples were collected. Whether or not the transformation was performed could be confirmed by the plant body showing a GFP fluorescence. The collected samples were quick-frozen with liquid nitrogen and then stored at −80° C. Since then, the tobacco leave samples were ground with a TissueLyser (QIAGEN), a buffer for extraction (125 mM of Tris-HCL pH 8.8, 1% SDS, 10% Glycerol, and 50 mM of $Na_2S_2O_5$) was added, supernatant was only isolated using a centrifuge, and then a western blotting analysis was performed using the supernatant. FIG. 7 shows a result of western blotting illustrating whether or not it was possible to normally express the fusion protein, in which a BRT tag was bound to N-terminal of GST protein, on a plant cell and it was possible to detect the fusion protein by the 2B8 antibody. As can be seen in FIG. 7, the fusion protein having the BRT tag ligated to the N-terminal of GFP was smoothly expressed regardless of the leaves growth in the plant cells, and the expressed protein was detected in a satisfactory level by the 2B8 antibody. In addition, the epitope tagging system using the BRT tag and 2B8 antibody exhibited the effect at an almost equal level as compared with the epitope tagging system using a c-myc tag that was generally used and an antibody thereto.

EXAMPLE 7

Figure 8:
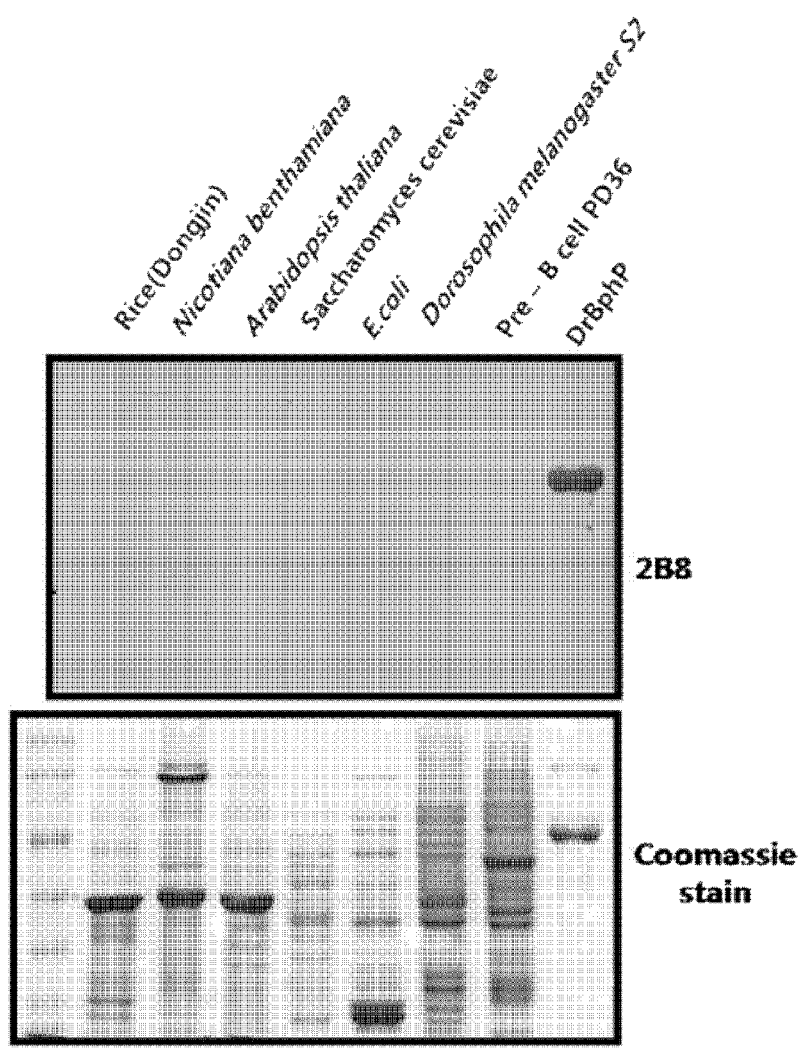
FIG. 8 shows a result of performing a western blotting using the 2B8 antibody to various kinds of cell proteins and a result of coomassie staining of the cell protein samples used in the western blotting.

Analysis Whether or Not BRT Tag or 2B8 Antibody was Non-Specifically Bound 7-1: Whether or Not 2B8 Antibody was Non-Specifically Bound to the Protein in Various Organism Cells In order to confirm whether or not the 2B8 antibody was non-specifically bound to the protein in cells of various species, the proteins extracted from rice (Variety: Dongjin), tobacco (Specific name: Nicotiana benthamiana), Arabidopsisthaliana, yeast (Specific name: Saccharomyces cerevisiae), E. coli, Drosophilamelanogaster S2, and a Pre-B cell PD36 were subjected to a western blotting. At this time, the purified DrBphP protein was used as a positive control and the crude extracts that were not processed through a further purification process were used as the other samples. Specifically, the rice (Variety: Dongjin), tobacco (Specific name: Nicotiana benthamiana), and Arabidopsisthaliana were frozen with liquid nitrogen; the frozen samples were ground; the ground samples were dissolved in a PBS buffer; the dissolved samples were centrifuged; the supernatants were extracted; and then the supernatants were used for the western blotting. In addition, in the case of the yeast (Specific name: Saccharomycescerevisiae) and E. coli, the cell cultures were centrifuged; the cells were collected; the collected cells were suspended in a PBS buffer; the suspended cells were sonicated to destroy the cells; the sonicated cells were again centrifuged to extract the supernatants; and then the supernatants were used for a western blotting. In addition, in the case of Drosophilamelanogaster S2 and Pre-B cell PD36, the cell cultures were centrifuged to collect cells; the collected cells were dissolved in a running sample buffer for a SDS-PAGE; and the dissolved cells were used. Furthermore, in order to confirm whether or not a loading of the protein sample used for the western blotting analysis was right, a coomssie staining was adjunctively performed. FIG. 8 shows a result of performing a western blotting using the 2B8 antibody to various kinds of cell proteins and a result of coomassie staining of the cell protein samples used in the western blotting. As can be seen in FIG. 8, the 2B8 antibody was specifically bound to the DrBphP protein including the BRT tag and there were no non-specific bindings between the proteins in cells of various species and the 2B8 antibody.

7-2: Whether or Not Epitope Tagging System Including BRT Tag and 2B8 Antibody was Non-Specifically Bound The fusion proteins having a BRT tag, Flag tag, His tag, and Myc tag respectively bound to the C-terminal of DrBphN modified protein without amino acids at 1 to 11 locations in a DrBphN protein (SEQ ID NO: 6) were expressed through culturing transformed cells, the total proteins were extracted, and then the expression aspects were observed through the western blotting. First, in order to clone DNA encoding the fusion protein having the BRT tag ligated to the C-terminal of the DrBphN modified protein (referred to as 12-321::BRT); DNA encoding the fusion protein having the Flag tag ligated to the C-terminal of the DrBphN modified protein (referred to as 12-321::Flag); DNA encoding the fusion protein having the His tag ligated to the C-terminal of the DrBphN modified protein (referred to as 12-321::His); and DNA encoding the fusion protein having the Myc tag ligated to the C-terminal of the DrBphN modified protein (referred to as 12-321::Myc), the respective primers were prepared. The primers used for performing a PCR for obtaining four amplification products are listed in the following Table 7. In the following Table 7, the primer as set forth in SEQ ID NO: 50 is a forward primer that was complementarily bound in the right direction starting from the base sequence of an amino acid at 12th location of the DrBphN protein, and a common primer for the rest four reverse primers. In addition, the primers as set forth in SEQ ID NOS: 51 to 54 included a tag base sequence respectively, and were reverse primers that were complementarily bound in the left direction starting from the base sequence of an amino acid at 321st location of the DrBphN protein. A PCR was performed 30 cycles using the prepared primers and PrimeSTAR HS (TAKARA, R040) polymerase, and a DrBphP DNA (SEQ ID NO: 5) was used as a template for the PCR. The desired DNA was only isolated from the amplified PCR products, and then ligated to a pJET (CloneJET PCR cloning kit, Fermentas, #K1232) vector. Since then, the base sequence was measured by asking the binding vector to Bioneer co.(KR). As a result, it was confirmed that the DNA products obtained from the PCR had the desired base sequences.

Table 7

TABLE 7

| SEQ ID NO: | Type of primer | Base sequence (5'→3') |
|---|---|---|
| 50 | Forward primer for cloning DrBphN modified protein 12-321 | CCATGGCA CCGCTTTACCTTGGTGGCCCG |
| 51 | Reverse primer for cloning 12-321::BRT | CTCGAG TCA CGGTG-GAAAAAAGGGCAACGGGTCCCG CGCTTC-CTTGACCTGAACTTG |
| 52 | Reverse primer for cloning 12-321::Flag | CTCGAG TCA CTTATCGTCGTCATC-CTTGTAATC CGCTTCCTTGACCTGAACTTG |
| 53 | Reverse primer for cloning 12-321::His | CTCGAG TCA GTGGTGGTGGTGGTGGTG CGCTTCCTTGACCTGAACTTG |
| 54 | Reverse primer for cloning 12-321::Myc | CTCGAG TCA TAAATCTTCTTCAGAAAT-TAATTTTTGTTC CGCTTCCTTGAC-CTGAACTTG |

Figure 9:
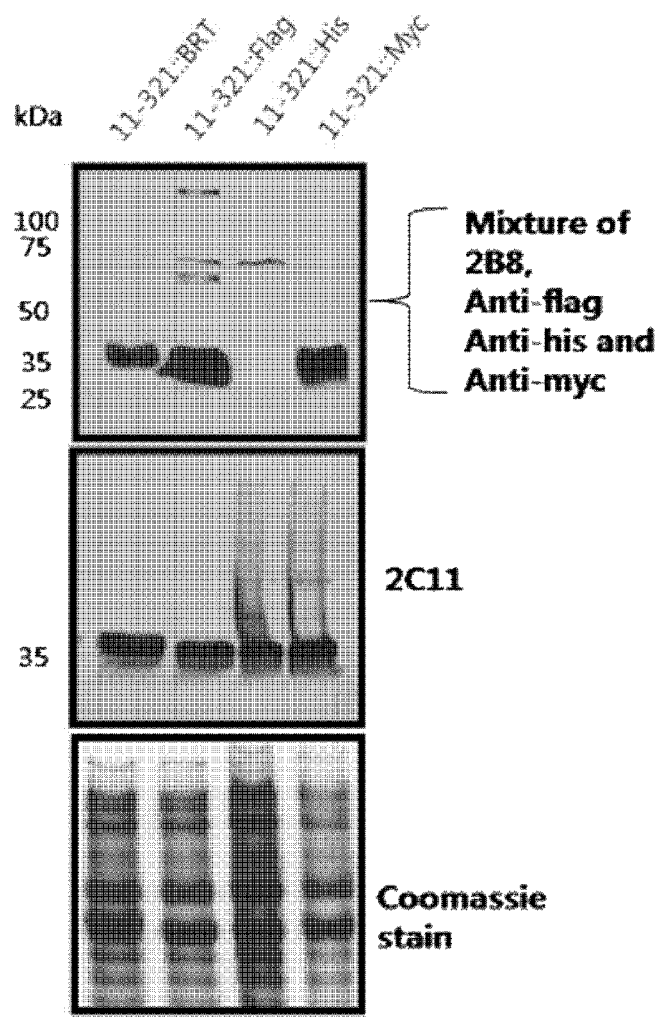
FIG. 9 shows results of observing expression aspects of total proteins through a western blotting after expressing the fusion proteins, in which a BRT tag, Flag tag, His tag, and Myc tag were respectively bound to C-terminals of DrBphN modified protein without amino acids of 1 to 11 locations in DrBphN protein (SEQ ID NO: 6), through a culture of transformed cells; and then extracting the total proteins, and results of coomassie staining of various fusion proteins samples used for the western blotting.

Since then, the amplified DNA products were respectively inserted a pET28a(+) vector (Manufacturer: Novagen) using a restriction enzyme, Nde I and Xho I, transformed to a BL21 competent cell (Manufacturer: RBC, Taipei, Taiwan), E. coli at 42° C. for 1 minute by applying heat shock, and cultured on a LB medium including kanamycin. The colonies transformed to the BL21 competent cell that were grown on the LB medium were inoculated to a LB medium including kanamycin, and then seed-cultured at 37° C. for about 8 hours. The seed-cultured cells were inoculated to the LB medium including kanamycin and cultured until reaching to 0.6 values at $OD_{600}$; IPTG (isopropyl-1-thio-β-D-galactopyranoside) was added to be a total concentration of 0.5 mM; and then the protein expression was induced at 25° C. for 6 hours. Since then, the cells were centrifuged, the supernatant was removed out, and then pellet was re-suspended in a binding buffer (100 mM of Tris-C1, 150 mM of NaCl and 10 mM of imidazole, pH 8.0). Then, the re-suspended pellet was sonicated to destroy cells, the sonicated pellet was again centrifuged to extract the supernatant, and then the supernatant was used for a western blotting analysis. At this time, the mixed antibodies prepared by mixing a 2B8 monoclonal antibody, anti-flag antibody, anti-his antibody, and anti-myc antibody were used as a primary antibody, and Horseradish peroxidase (HRP) conjugated anti-mouse immunoglobulin (anti-mouse IgG; Sigma) was used as a secondary antibody. In addition, in order to develop the samples transferred to the cellulose membrane after performing a SDS-PAGE, Amersham™ ECL™ Western Blotting Detection Reagents (GE Healthcare, RPN2106OL/AF) was used. Meanwhile, in order to confirm the expression of DrBphN modified protein, a western blotting was performed by using a 2C11 antibody, other monoclonal antibody, capable of confirming a DrBphN protein, as a primary antibody. In addition, in order to confirm whether or not a loading of protein sample used for the western blotting analysis was right, a coomassie staining was adjunctively performed. FIG. 9 shows a result of observing expression aspect of total proteins through a western blotting after expressing the fusion proteins, in which a BRT tag, Flag tag, His tag, and Myc tag were respectively bound to C-terminals of DrBphN modified protein without amino acids of 1 to 11 sites in DrBphN protein (SEQ ID NO: 6), through a culture of transformed cells; and then extracting the total proteins, and a result of coomassie staining of various fusion proteins samples using the western blotting. As can be seen in FIG. 9, it could be confirmed from the western blotting result using the 2C11 antibody that the sizes of the fusion proteins having the BRT tag, Flag tag, His tag, and Myc tag respectively ligated to the C-terminal of the DrBphN modified protein was about 35 kDa. In addition, it was considered that the expression amount of BRT tag ligated to the C-terminal of the DrBphN modified protein was good and the BRT tag was specifically bound to the 2B8 antibody. However, in the case of expressing the His tag ligated to the C-terminal of the DrBphN modified protein, the His tag was not detected by using an anti-his antibody, and in the case of the His tag and Flag tag, the non-specific bands not corresponding to the respective antibodies were detected.

As described above, the present invention was described through the above Examples, but the present invention is not limited thereto. It can be considered that various modifications can be performed within the scope and range of the present invention. Therefore, it should be understood that the range of the present invention include all the embodiments belonging to the range of claims in the present invention.

*a deposit certificate of hybridoma cell line KCTC 12283BP

BUDAPEST TREATY ON THE INTERNATIONAL RECOGNITION OF THE DEPOSIT
OF MICROORGANISMS FOR THE PURPOSE OF PATENT PROCEDURE

INTERNATIONAL FORM

RECEIPT IN THE CASE OF AN ORIGINAL DEPOSIT issued pursuant to Rule 7.1

TO : BHOO, Seong Hee
Graduate School of Biotechnology and Plant Metabolism Research Center, Kyung Hee University
1732 Deokyoungdaero, Giheung-gu, Yongin-si, Gyeonggi-do, 446-701
Republic of Korea

| I. IDENTIFICATION OF THE MICROORGANISM | |
|---|---|
| Identification reference given by the DEPOSITOR:<br><br>2B8<br>(animal cell line) | Accession number given by the INTERNATIONAL DEPOSITARY AUTHORITY:<br><br>KCTC 12283BP |

| II. SCIENTIFIC DESCRIPTION AND/OR PROPOSED TAXONOMIC DESIGNATION |
|---|
| The microorganism identified under I above was accompanied by:<br>[ x ] a scientific description<br>[   ] a proposed taxonomic designation<br>(Mark with a cross where applicable) |

| III. RECEIPT AND ACCEPTANCE |
|---|
| This International Depositary Authority accepts the microorganism identified under I above, which was received by it on September 24, 2012. |

| IV. RECEIPT OF REQUEST FOR CONVERSION |
|---|
| The microorganism identified under I above was received by this International Depositary Authority on                     and a request to convert the original deposit to a deposit under the Budapest Treaty was received by it on |

| V. INTERNATIONAL DEPOSITARY AUTHORITY | |
|---|---|
| Name: Korean Collection for Type Cultures<br><br>Address: Korea Research Institute of Bioscience and Biotechnology (KRIBB)<br>125 Gwahak-ro, Yuseong-gu,<br>Daejeon 305-806<br>Republic of Korea | Signature(s) of person(s) having the power to represent the International Depositary Authority of authorized official(s):<br><br>BAE, Kyung Sook, Director<br>Date: October 5, 2012 |

The invention claimed is:

1. A peptide tag consisting of the amino acid sequence as set forth in SEQ ID NO: 2.

2. A fusion protein comprising a target protein and a peptide tag heterologous to the target protein and bound to the target protein, the peptide tag consisting of the amino acid sequence as set forth in SEQ ID NO: 1 or as set forth in SEQ ID NO: 2.

3. A method for detecting a fusion protein, the method comprising contacting and binding the fusion protein according to claim 2 to an antibody to the peptide tag consisting of the amino acid sequence set forth in SEQ ID NO:1 or as set forth in SEQ ID NO: 2; and confirming whether or not the fusion protein bound to the antibody is present; or analyzing an amount of the fusion protein bound to the antibody, thereby detecting the fusion protein.

4. A method for purifying a fusion protein, the method comprising;

providing a sample comprising the fusion protein of claim 2;

contacting and binding the fusion protein according to claim 2 to an antibody to the peptide tag consisting of the amino acid sequence set forth in SEQ ID NO:1 or as set forth in SEQ ID NO: 2; and collecting the fusion protein bound to the antibody, thereby purifying the fusion protein from the sample.

* * * * *